(12) United States Patent
Mahmood et al.

(10) Patent No.: US 12,230,399 B2
(45) Date of Patent: Feb. 18, 2025

(54) MULTIMODAL FUSION FOR DIAGNOSIS, PROGNOSIS, AND THERAPEUTIC RESPONSE PREDICTION

(71) Applicant: THE BRIGHAM AND WOMEN'S HOSPITAL, INC., Boston, MA (US)

(72) Inventors: Faisal Mahmood, Brookline, MA (US); Richard Chen, Gaithersburg, MD (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 305 days.

(21) Appl. No.: 17/762,125

(22) PCT Filed: Sep. 28, 2020

(86) PCT No.: PCT/US2020/053079
§ 371 (c)(1),
(2) Date: Mar. 21, 2022

(87) PCT Pub. No.: WO2021/062366
PCT Pub. Date: Apr. 1, 2021

(65) Prior Publication Data
US 2022/0367053 A1    Nov. 17, 2022

Related U.S. Application Data

(60) Provisional application No. 62/907,096, filed on Sep. 27, 2019.

(51) Int. Cl.
*G16H 50/20*       (2018.01)
*G06T 7/00*        (2017.01)
(Continued)

(52) U.S. Cl.
CPC .......... *G16H 50/20* (2018.01); *G06T 7/0012* (2013.01); *G06V 10/806* (2022.01);
(Continued)

(58) Field of Classification Search
None
See application file for complete search history.

(56) References Cited

U.S. PATENT DOCUMENTS 10,248,664 B1 *   4/2019   Shen .................. G06N 5/046
10,496,884 B1 *   12/2019  Nguyen ............... G06V 30/413
(Continued)

FOREIGN PATENT DOCUMENTS

CN    201810049756 A   *   1/2018   ............... G06K 9/62

OTHER PUBLICATIONS

Pathomic Fusion: An Integrated Framework for Fusing Histopathology and Genomic Features for Cancer Diagnosis and Prognosis by Chen et al., PatharXiv: 1912.08937v3 [cs.CV] Sep. 3, 2020.*
(Continued)

*Primary Examiner* — David J Stoltenberg
(74) *Attorney, Agent, or Firm* — Tarolli, Sundheim, Covell & Tummino LLP

(57) ABSTRACT

Systems and methods can quantify the tumor microenvironment for diagnosis, prognosis and therapeutic response prediction by fusing different data types (e.g., morphological information from histology and molecular information from omics) using an algorithm that harnesses deep learning. The algorithm employs tensor fusion to provide end-to-end multimodal fusion to model the pairwise interactions of features across multiple modalities (e.g., histology and molecular features) and deep learning. The systems and methods improve upon traditional methods for quantifying the tumor microenvironment that rely on concatenation of extracted features.

17 Claims, 19 Drawing Sheets

(51) Int. Cl.
    *G06V 10/80*    (2022.01)
    *G06V 20/69*    (2022.01)
    *G16B 30/00*    (2019.01)
    *G16B 40/20*    (2019.01)
(52) U.S. Cl.
    CPC .......... *G06V 20/695* (2022.01); *G16B 30/00* (2019.02); *G16B 40/20* (2019.02); *G06T 2207/10056* (2013.01); *G06T 2207/20036* (2013.01); *G06T 2207/20081* (2013.01); *G06T 2207/20221* (2013.01); *G06T 2207/30096* (2013.01); *G06V 2201/03* (2022.01)

(56) References Cited

U.S. PATENT DOCUMENTS

| | | | |
|---|---|---|---|
| 2014/0233826 A1 | 8/2014 | Agaian et al. | |
| 2014/0235474 A1* | 8/2014 | Tang | C12Q 1/6869 702/19 |
| 2018/0122507 A1* | 5/2018 | Alter | G16B 50/20 |
| 2019/0024434 A1 | 8/2019 | Matias et al. | |
| 2019/0244348 A1* | 8/2019 | Buckler | G06V 20/69 |
| 2020/0175095 A1* | 6/2020 | Morariu | G06N 3/045 |
| 2020/0294622 A1* | 9/2020 | Szeto | G16B 40/30 |
| 2020/0303078 A1* | 9/2020 | Mayhew | G06N 20/10 |
| 2021/0319907 A1* | 10/2021 | Harley | G16H 50/70 |
| 2021/0381058 A1* | 12/2021 | Szeto | G01N 33/56972 |
| 2022/0359077 A1* | 11/2022 | Chorev | G06V 20/695 |

OTHER PUBLICATIONS

See Manzoni et al. Genome, transcriptome and proteome: the rise of omics data and their integration in biomedical sciences, Briefings in Bioinformatics, 19(2), 2018, 286-302 doi: 10.1093/bib/bbw114, Advance Access Publication Date: Nov. 22, 2016.*
Guillermo de Anda-Jáuregui et al., Computational Oncology in the Multi-Omics Era: State of the Art, Frontiers in Oncology, Apr. 2020, vol. 10, Article 423.*
Data Fusion in Metabolomics Using Coupled Matrix and Tensor Factorizations; Acar et al., Proceedings of the IEEE | vol. 103, No. 9, Sep. 2015.*
Sun et al. Dynamic Tensor Clustering, arXiv:1708.07259v2 [stat. ML] Sep. 14, 2018.*
International Search Report for Corresponding Application Serial No. PCT/US20/53079.

* cited by examiner

FIG. 8

MULTIMODAL FUSION FOR DIAGNOSIS, PROGNOSIS, AND THERAPEUTIC RESPONSE PREDICTION

CROSS-REFERENCE TO RELATED APPLICATIONS

This application claims the benefit of U.S. Provisional Application No. 62/907,096, filed Sep. 27, 2019, entitled "MULTIMODAL FUSION OF HISTOLOGY AND MOLECULAR FEATURES FOR CANCER DIAGNOSIS, PROGNOSIS, and SURVIVAL PREDICTION". This provisional application is hereby incorporated by reference in its entirety for all purposes.

TECHNICAL FIELD

The present disclosure relates generally to the tumor microenvironment and, more particularly, to systems and methods that quantify the tumor microenvironment by fusing different data types (e.g., morphological information from histology and molecular information from omics) using an algorithm that harnesses deep learning.

BACKGROUND

Oncologists often rely on heterogeneous data sources including qualitative information from histology (e.g., morphological information) and quantitative information from genetic data (e.g., molecular information) to predict clinical outcomes. In fact, histology-based subjective and qualitative analysis of the tumor microenvironment coupled with quantitative examination of genomic assays is the standard-of-care for most cancers in modern clinical settings, but the histopathology and genetic analysis are performed separately. As the field of atomic pathology migrates from glass slides to digitized whole slide histology images, there is a critical opportunity to develop algorithmic approaches that combine digitized histology images and genetic data (e.g., providing phenotypic and genotypic information) in an integrative manner. Current algorithmic approaches have relied on concatenation of extracted feature vectors, which have only demonstrated marginal improvement compared to traditional analytics.

SUMMARY

The present disclosure relates to systems and methods that employ a new algorithmic approach that fuses different data types (e.g., morphological information from histology and molecular information from omics) in an integrative manner to quantify the tumor microenvironment. Such quantification of the tumor microenvironment can provide information (e.g., one or more biomarkers) useful for cancer diagnosis, prognosis, patient stratification, survival prediction, therapeutic response prediction, resistance prediction, and the like. The algorithmic approach is scalable and interpretable for multiple modalities of different data types and harnesses deep learning. Tensor fusion is used to integrate the different data types (e.g., histology and molecular feature analytics) and provide end-to-end multimodal fusion to explicitly model the pairwise interactions of features across multiple modalities in connection with multimodal learning, which improves upon current approaches that rely on concatenation of extracted features.

In one aspect, the present disclosure can include a system that employ multimodal fusion of histology and molecular (genomic, transcriptomic etc.) features to improve cancer diagnosis, prognosis, survival prediction, and the like. The system can include at least a computing device and a display device. The computing device can include a memory storing instructions; and a processor configured to access the memory to execute the instructions to at least: receive histopathology information related to a diseased portion of a subject and omics data related to the diseased portion of the subject; determine a first matrix of histology features from the histopathology information, wherein the histology features are of a first data type, wherein the first matrix is of a first size; determine a second matrix of molecular features from the omics data, wherein the molecular features are of a second data type, wherein the second matrix is of a second size; fuse the histology features and the molecular features to form a third matrix; determine a prognosis, and/or a therapeutic response profile for the diseased portion of the subject based on at least a portion of the third matrix; and output the diagnosis, the prognosis, and/or the therapeutic response profile for the diseased portion of the subject to the display device. The display device can be configured to display the diagnosis, the prognosis, and/or the therapeutic response profile for the diseased portion of the subject based on the fused histology features and molecular features.

In another aspect, the present disclosure can include a method for employing multimodal fusion of histology and molecular features to improve cancer diagnosis, prognosis, survival prediction, and the like. The method can be executed by a system comprising a processor. Histopathology information related to a diseased portion of a subject and omics data related to the diseased portion of the subject can be received. A first matrix of a first size of histology features of a first data type from the histopathology information (also referred to as morphologic information) and a second matrix of a second size of molecular features of a second data type from the ohmic information can be determined. The histology features and the molecular features can be fused to form a third matrix. A diagnosis, a prognosis, and/or a therapeutic response profile for the diseased portion of the subject cam be determined and output based on at least a portion of the third matrix.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 7-9 show illustrations related to glioblastoma and lower grade glioma;

DETAILED DESCRIPTION

Definitions

Figure 1:
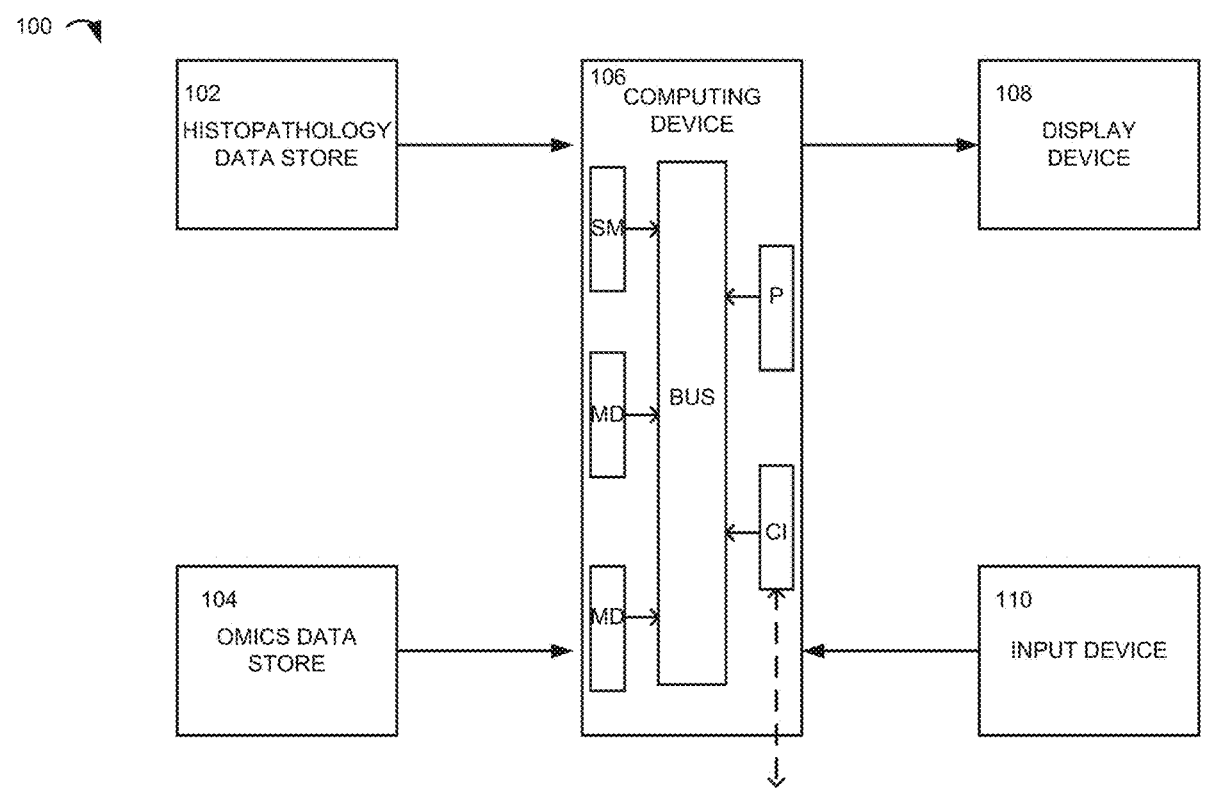
FIG. 1 is a diagram illustrating a system that quantifies the tumor microenvironment by fusing different data types (e.g., morphological information from histology and molecular information from omics) using an algorithm that harnesses deep learning, according to an aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

The sequence of operations (or acts/steps) is not limited to the order presented in the claims or figures unless specifically indicated otherwise.

As used herein, the term "fusion" refers to the process of integrating information from various input modalities (e.g., histopathology information and molecular features from genetic information) and combining them into a single output (e.g., a diagnosis, a prognosis, a therapeutic response profile, or the like). Pathomic Fusion is a type of fusion described herein that relates to a framework for multimodal fusion of histology and genomic features as pairwise feature interactions across modalities by taking the Kronecher product of gated feature representations, and controls the expressiveness of each representation using a gating-based attention mechanism.

As used herein, the term "histology" refers to the study of the microscopic structure of tissues (e.g., from a biopsy, surgical specimen, or the like). This study can be done by a pathologist after the specimen has been processed (which may be done automatically) and may include microscopic examination of the specimen.

As used herein, the term "whole-slide images" can refer to high-resolution images of slides produced by the scanning/digitization of a complete conventional glass microscope slide. The whole-slide images can be a type of histopathology information.

As used herein, the term "omics" refers to the collective technologies used to explore the roles, relationships, and actions of the various types of molecules that make up the cells of an organism. Generally, omics can include genomics, proteomics, transcriptomics, and/or metabolomics.

As used herein, the term "molecular features" refers to features that are seen on a molecular level, including for example the structure of DNA, RNA, and proteins, genotypic data, phenotypic data, or the like.

As used herein, the term "transcriptome profiling" refers to a tool that can expose expression patterns in RNA to define cellular states or to identify genes with similar expression patterns. Methods of profiling include, for example: microarrays, Serial Analysis of Gene Expression (SAGE), RNA sequencing (RNA-Seq), and Massively Parallel Signature Sequencing (MPSS). The results of these methods, and others, is a transcriptome profile.

As used herein, the term "transcriptome" refers to the set of all RNA molecules in one cell or a population of cells. In some instances, a transcriptome can also refer to only mRNA.

As used herein, the term "morphological features" refers to the study of the form and structure of an organism as a whole, including all internal and external structures. These structures can be referred to as morphological features.

As used herein, the term "field programmable gate array (FPGA)" refers to an integrated circuit that contains an array of programmable logic blocks and a hierarchy of reconfigurable interconnects that allow the blocks to be wired together to perform simple logic or complex combinatorial functions.

As used herein, the term "deep learning" refers to a subset of machine learning in artificial intelligence that has networks capable of learning unsupervised from data that is unstructured or unlabeled using multiple layers to progressively extract higher level features from the raw input. Deep learning can also be known as deep neural learning or deep neural network. Modern deep learning models are often based on artificial neural networks, which can include, but are not limited to: Convolutional Neural Networks (CNNs), Graph Convolution Networks (GCNs), Survival Neural Networks (SNNs), and Tensor Fusion Networks.

As used herein, the term "tensor fusion network" refers to a strategy for multimodal fusion of molecular and histology features which calculates the outer product space of feature embeddings to explicitly model the pairwise interactions of all features across modalities.

As used herein, the term "end-to-end multimodal learning" refers to training a possible complex learning system by applying gradient-based learning to the system as a whole. The entire process involves a single, layered or recurrent neural network without modularization, and is trained by reinforcement learning.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

Overview

The present disclosure relates generally to the tumor microenvironment, a complex milieu of cells containing cancer cells, immune cells, stromal cells, and healthy cells. Though histologic analysis of tissue provides important spatial and morphological information of the tumor microenvironment, the qualitative inspection by human pathologists has been shown to suffer from large interobserver and intraobserver variability. Moreover, subjective interpretation of histology slides does not make use of the rich molecular information (e.g., genetic information, such as phenotypic information) that has shown to have prognostic relevance. Genomic analysis of tissue biopsies can provide quantitative information on genomic expression and alterations, but cannot precisely isolate tumor-induced genotypic measures and changes from those of non-tumor entities, such as normal cells. Sequencing technologies, like single cell sequencing, are able to resolve genomic information of individual cells in tumor specimens, with spatial transcriptomics and multiplexed immunofluorescence able to spatially resolve histology tissue and genomics together, but these technologies lack clinical penetration and do not explicitly incorporate information from the spatial organization and community structure of cells, which have known diagnostic and prognostic relevance (e.g., for cancer diagnosis, prognosis, patient stratification, survival prediction, therapeutic response prediction, resistance prediction, and the like).

Fusing different data types (e.g., morphological information from histology and molecular information from omics) can better quantify the tumor microenvironment and harness deep learning for the development of assays for early diagnosis, prognosis, patient stratification, survival, therapeutic response, resistance prediction, and the like. Employing deep learning, such multimodal fusion has emerged as an interdisciplinary, computational field that seeks to correlate and combine disparate heterogenous data sources to solve difficult supervised learning tasks. Accordingly, the present disclosure relates to systems and methods that employ a new algorithmic approach that harnesses deep learning to employ multimodal fusion to fuse different data types (e.g., morphological information from histology and molecular information from genomics) in an integrative manner to quantify the tumor microenvironment. The algorithmic approach employs an end-to-end fusion of molecular and histology features to explicitly model the pairwise interactions of features across multiple modalities. Previous algorithmic solutions integrate histopathology images and molecular features by relying on the concatenation of extracted feature embeddings from separately trained deep networks. Though technically projected into a shared subspace, fusion representations via vector concatenation do not model any pairwise interaction between features of the respective modalities, such as the inter-modality dynamics of genomic signatures and histology image markers. A strategy for multimodal fusion of molecular and histology features called Tensor Fusion is employed by the systems and methods described herein, which calculates the outer product space of feature embeddings to explicitly models the pairwise interactions of all features across modalities, improving on previous solutions that utilize vector concatenation for early diagnosis, prognosis, patient stratification, survival, therapeutic response and resistance prediction.

Systems

One aspect of the present disclosure includes a system 100 that can quantify the tumor microenvironment by fusing different data types (e.g., morphological information from histology and molecular information from omics, but can include more and/or alternate data types) using an algorithm that harnesses deep learning. The algorithm, which can also be referred to as Pathomic Fusion, cam fuse the different data types into a multimodal tensor that explicitly models bimodal and trimodal interactions from each modality that provides the different data types. The multimodal tensor can be used in medicine for fine-grained patient stratification and interpreted for finding prognostic features.

The system 100 can employ multimodal fusion of histology and molecular features using the algorithm known as Pathomic Fusion to improve cancer diagnosis, prognosis, survival prediction, and the like. The system 10 includes a histopathology data store 102, an omics data store 104, a computing device 106, a display device 108 to display data and parameters to a user (e.g., a video screen), and may include one or more input device 110 to allow the user to interact with the system 100 (e.g., a keyboard, touch screen, and/or a mouse). In some instances, two or more of the components of the system 10 can be within and/or linked together by a common device, such as a field programmable gate array (FPGA).

As one example, the histopathology data store 102 can include one or more non-transitory memories that store data related to one or more histology studies of a diseased portion of a patient and can provide at least a portion of the data to the computing device 106. The omics data store 104 can include one or more non-transitory memories that store data related to one or more "ohmic", such as genomics, proteomics, transcriptomics, metabolomics, or the like, studies of at least a portion of the patient, such as the diseased portion of the patient and can provide at least a portion of the data to the computing device 106. In some instances, the histopathology data store 102 and the omics data store 104 can be remote from one another (one of which may be local to the computing device 106). In other instances, the histopathology data store 102 and the omics data store 104 can be part of a common device (which can be local or remote to the computing device 106). Additionally, the term "data store" may also be expressed as a memory, device, apparatus, or the like.

The computing device 106 of FIG. 1 is an example of one or more hardware devices that can be part of the system 100 and capable of implementing the systems and methods described herein. The computing device 106 can include various systems and subsystems and can be a personal computer, a laptop computer, a workstation, a computer system, an application-specific integrated circuit (ASIC), a server BladeCenter, a server farm, etc.

The computing device 106 is schematically illustrated as block diagrams with the different blocks representing different components. The computing device 106 can include a system bus (BUS), a processing unit (P), a system memory (SM), memory devices (MDs), a communication interface (CI) (e.g., a network interface, which may be in communication with a network-potentially with the histopathology data store 102 and/or the omics data store 104, represented as a dashed line). The system bus (BUS) can be in communication with the processing unit (P) and the system memory (SM). The additional memory devices (MDs), such as a hard disk drive, server, standalone database, or other non-volatile memory, which may be unnecessary and/or may include the histopathology data store 102 and/or the omics data store 104, can also be in communication with the system bus (BUS). The system bus (BUS) interconnects the processing unit (P), the memory devices (SM and MDs), and the communication interface (CI). The system bus (BUS) may also be in communication with the display device 108, and the input device 110. In some examples, the system bus (BUS) also interconnects an additional port (not shown), such as a universal serial bus (USB) port.

The processing unit (P) can be a computing device and can include an application-specific integrated circuit (ASIC). The processing unit (also referred to as processor 204) executes a set of instructions to implement the operations of examples disclosed herein. The processing unit can include a processing core. Moreover, as described herein, the term "storage medium" and memory device" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

The memory devices (SM, MDs) can store data, programs, instructions, database queries in text or compiled form, and any other information that may be needed to operate a computer. The memory devices (SM, MDs) can be implemented as computer-readable media (integrated or removable), such as a memory card, disk drive, compact disk (CD), or server accessible over a network. In certain examples, the memory devices (SM, MDs) can comprise text, images, video, and/or audio, portions of which can be available in formats comprehensible to human beings. Additionally or alternatively, the system 100 can access an external data source or query source through the communication interface (CI), which can communicate with the system bus (SB) and the communication link (dashed line).

In operation, the computing device 106 (shown as the memory 202 and processor 204 in FIG. 2) can be used to implement one or more parts of a system 100, such as that illustrated in FIG. 1. Computer executable logic for implementing the system resides on one or more of the system memory (SM), and the memory devices (MDs) in accordance with certain examples. The processing unit (P) executes one or more computer executable instructions originating from the system memory (SM), and the memory devices (MDs). The term "computer readable medium" as used herein refers to a medium that participates in providing instructions to the processing unit (P) for execution. This medium may be distributed across multiple discrete assemblies all operatively connected to a common processor or set of related processors.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the systems and methods can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, systems and methods can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Figure 2:
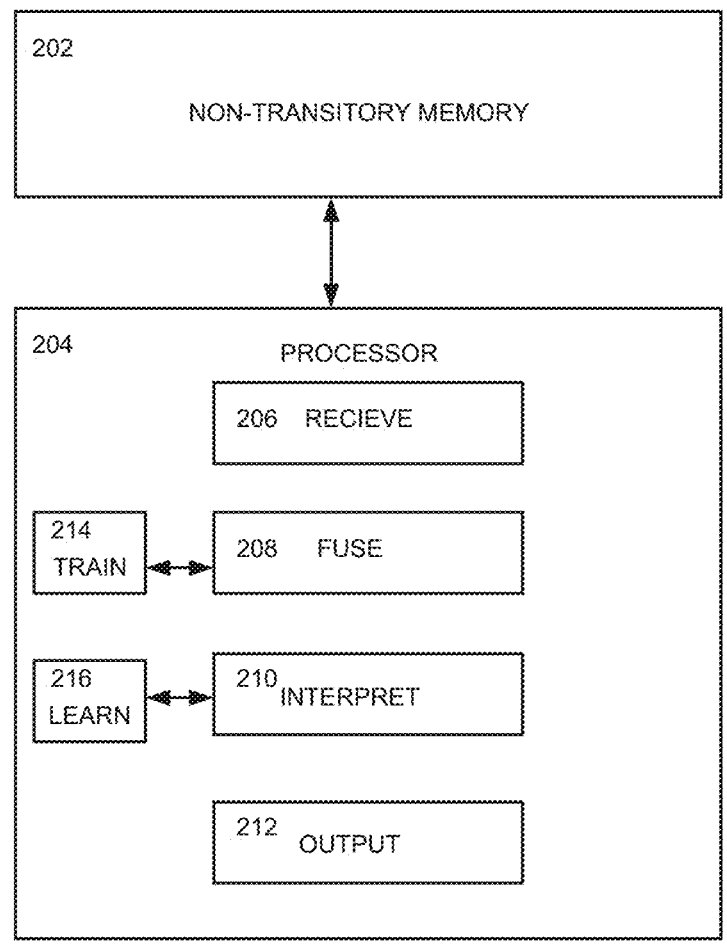
FIG. 2 is a diagram illustrating an example of the computing device of FIG. 1.

FIG. 2 shows an example implementation 200 of the Pathomic Fusion algorithm by computing device 106. The Pathomic Fusion algorithm is implemented as a set of instructions (e.g., computer program instructions) stored in a non-transitory memory 202 (e.g., one or more of the system memory (SM) and the other memory devices (MDs)) and executable by a processor 204 (e.g., processor (P)). The processor 204 can be configured to access the memory 202 to execute the instructions (illustrated as components in FIG. 2) to create a mechanism for implementing the functions of the components, causing a series of operational steps to be performed on the computer or other programmable apparatus to produce a computer-implemented process such that the instructions that execute on the computer or other programmable apparatus provide steps for implementing the functions of the components specified in the block diagrams and the associated description.

Instructions executed by the processor 204 can include receive 206 histopathology information (e.g., at least one histopathology whole-slide image) related to a diseased portion of a subject (e.g., from histopathology data store 102) and omics data (e.g., including a transcriptome profile) related to the diseased portion of the subject (from omics data store 104); fuse 208 histology features from the histopathology information (also referred to as morphological information) and molecular features from the omics data; interpret 210 the fused data to determine a determine a prognosis, and/or a therapeutic response profile for the diseased portion of the subject; and output 212 the diagnosis, the prognosis, the therapeutic response profile, or the like, for the diseased portion of the subject (to display device 108) based on the fused histology features and molecular features. The display device 108 can display the diagnosis, the prognosis, the therapeutic response profile, or the like, for the diseased portion of the subject. The histopathology data store 102 and the omics data store 104 can acquire the histopathology information and the omics data and, in some instances, perform initial processing on the data. The initial processing can include determining a first matrix of a first size of histology features from the histology information (a first data type) and determining a second matrix of a second size of molecular features (a different second data type). The first matrix and the second matrix (and any other matrix) can be fused during fuse step 208. It should be noted that the fuse step 208 can be trained 214 based on a certain medical condition that the diseased portion of the subject has or is suspected of having. As one example, clustering attention multiple instance learning can be used to process an entirety of the whole slide histology image. Results of the interpret step 210 can be learned 216, as well as the condition of the subject. The training 214 and/or the learning 216 can use historical components stored in the non-transitory memory 202 and/or stored remotely. As an example, the training 214 and/or the learning 216 can employ a machine learning model (stored in the non-transitory memory 202 and executed by the processor 204) that generates a parameter representing, for example, the diagnosis, the prognosis, the probability that the patient will respond to treatment or the like.

For example, the machine learning model can train the fuse step 208 on training data representing the various classes of interest (e.g., the particular disease). For example, in supervised learning models, a set of examples having labels representing a desired output of the machine learning model can be used to train the system. The training process of the machine learning model will vary with its implementation, but training generally involves a statistical aggregation of training data into one or more parameters associated with the output classes. For rule-based models, such as decision trees, domain knowledge, for example, as provided by one or more human experts, can be used in place of or to supplement training data in selecting rules for classifying a user using the extracted features. Any of a variety of techniques can be utilized for the models, including support vector machines, regression models, self-organized maps, k-nearest neighbor classification or regression, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a radial basis function, although the systems and methods described herein can utilize any of a number of linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

The classical ANN classifier is fully-connected and feedforward. Convolutional neural networks, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A k-nearest neighbor model populates a feature space with labelled training samples, represented as feature vectors in the feature space. In a classifier model, the training samples are labelled with their associated class, and in a regression model, the training samples are labelled with a value for the dependent variable in the regression. When a new feature vector is provided, a distance metric between the new feature vector and at least a subset of the feature vectors representing the labelled training samples is generated. The labelled training samples are then ranked according to the distance of their feature vectors from the new feature vector, and a number, k, of training samples having the smallest distance from the new feature vector are selected as the nearest neighbors to the new feature vector.

In one example of a classifier model, the class represented by the most labelled training samples in the k nearest neighbors is selected as the class for the new feature vector. In another example, each of the nearest neighbors can be represented by a weight assigned according to their distance from the new feature vector, with the class having the largest aggregate weight assigned to the new feature vector. In a regression model, the dependent variable for the new feature vector can be assigned as the average (e.g., arithmetic mean) of the dependent variables for the k nearest neighbors. As with the classification, this average can be a weighted average using weights assigned according to the distance of the nearest neighbors from the new feature vector. It will be appreciated that k is a metaparameter of the model that is selected according to the specific implementation. The distance metric used to select the nearest neighbors can include a Euclidean distance, a Manhattan distance, or a Mahalanobis distance.

A regression model applies a set of weights to various functions of the extracted features, most commonly linear functions, to provide a continuous result. In general, regression features can be categorical, represented, for example, as zero or one, or continuous. In a logistic regression, the output of the model represents the log odds that the source of the extracted features is a member of a given class. In a binary classification task, these log odds can be used directly as a confidence value for class membership or converted via the logistic function to a probability of class membership given the extracted features.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decision trees that select a given task.

The fuse step 208 explicitly models pairwise interactions between the histology features and the molecular features to determine the third matrix. The histology features and the molecular features are fused by taking a Kronecher product of the first matrix and the second matrix to form the third matrix (which can be a block matrix). The fusing can include a tensor fusion process that calculates an outer product space of the histology features and the molecular features. The tensor fusion process can create a joint multimodal tensor cube (e.g., the third matrix) where every molecular feature is multiplied by every histopathology feature. The tensor fusion process performs the end-to-end multimodal learning with multimodal tensors as input supervised by a previously defined objective. The previously defined objective can be, for example, the diagnosis, the prognosis, and/or the therapeutic response profile for the diseased portion of the subject. The end-to-end multimodal fusion explicitly models pairwise interactions between the histology features and the molecular features.

Figure 3:
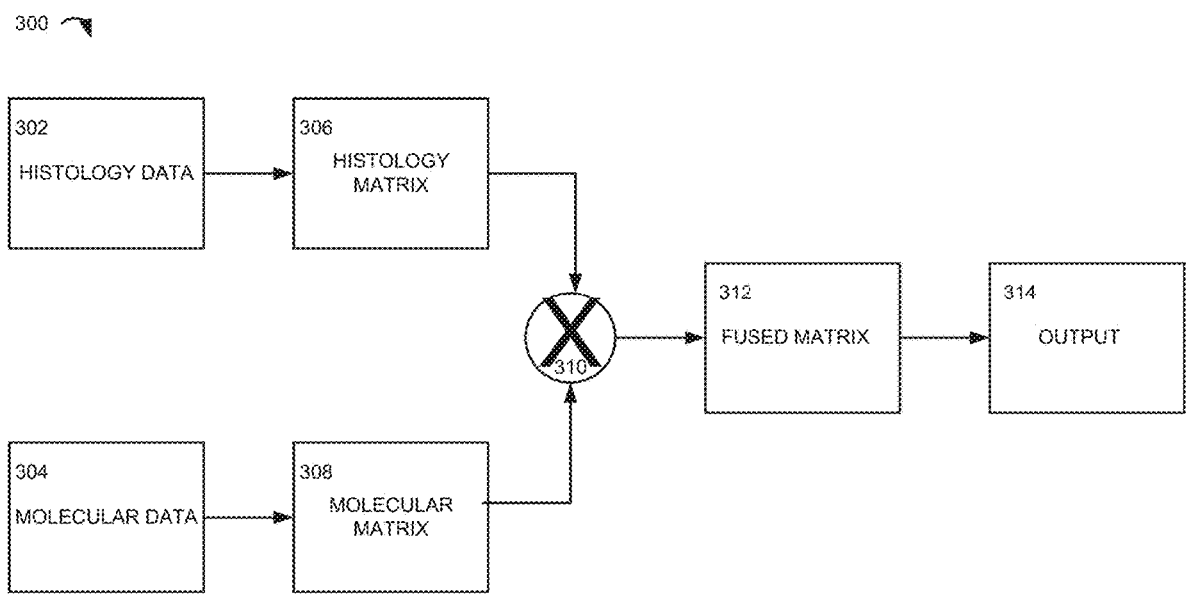
FIG. 3 is a diagram illustrating an example fusion of histology data and molecular data.
Figure 4:
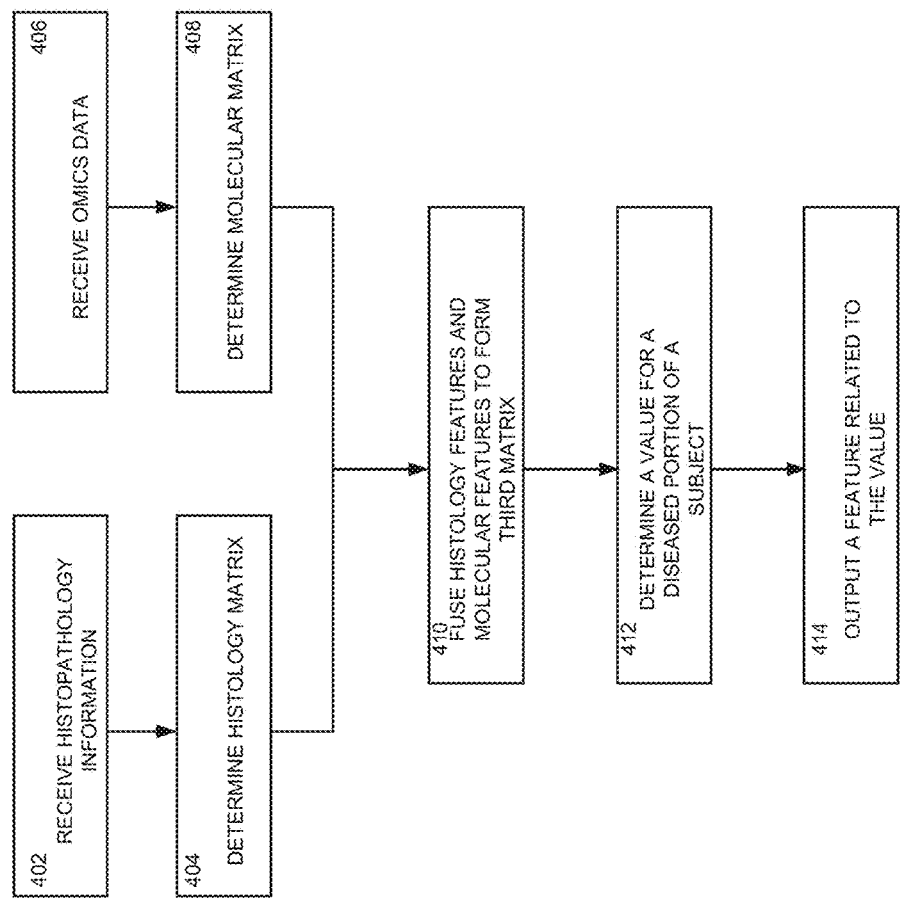
FIG. 4 is a process flow diagram illustrating a method for quantifying the tumor microenvironment by fusing different data types (e.g., morphological information from histology and molecular information from omics) using an algorithm that harnesses deep learning, according to another aspect of the present disclosure.

An example fusion 300 of histology data 302 and molecular data 304 is shown in FIG. 3. A histology matrix 308 is formed from the histology data 302. A molecular matrix 308 is formed from the molecular data 304. A tensor fusion 310 process can be completed between the histology matrix 306 and the molecular matrix 308 to provide a fused matrix 312 (which is a cube matrix). An output can be based on at least a portion of the fused matrix 312.

Methods

Another aspect of the present disclosure can include a method 40 for quantifying the tumor microenvironment by fusing different data types (e.g., morphological information from histology and molecular information from omics) using an algorithm that harnesses deep learning (FIG. 2). The algorithm may also be referred to as Pathomic Fusion. It should be noted that the method 20 may be performed using the components of the system 10, for example.

The method 40 is illustrated as process flow diagrams with flowchart illustrations. For purposes of simplicity, the method 40 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 40.

One or more blocks of the respective flowchart illustrations, and combinations of blocks in the flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The method 40 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

At 402, histopathology information related to a diseased portion of a subject can be received. The histopathology information can be related to at least one histopathology whole-slide image of at least part of a diseased portion of the subject. At 404, a histopathology matrix (or first matrix of a first size that includes histology features, also referred to as molecular features) can be determined from the histopathology information. The first matrix can include data of a first data type.

At 406, omics data (e.g., including a transcriptome profile) related to the diseased portion of the subject can be received. At 408, a molecular matrix (or second matrix of a second size that includes molecular features) can be determined from the omics data. The second matrix can include data of a second data type.

At 410, the histology features and molecular features (of different data types in matrices of different sizes) can be fused to form a third matrix (e.g., taking a Kronecher product of the first matrix and the second matrix to form the third matrix, where the third matrix is a block matrix). The fusing can include a tensor fusion process that calculates an outer product space of the histology features and the molecular features. The tensor fusion process can create a joint multimodal tensor cube where every molecular feature is multiplied by every histopathology feature. The third matrix can explicitly model pairwise interactions between the histology features and the molecular features.

At 412, a value can be determined for a diseased portion of a subject. For example, the value can be related to or indicative of a diagnosis, a prognosis, a therapeutic response profile, or the like, for the diseased portion of the subject based on at least a portion of the fused histology features and molecular features. For example, the tensor fusion can be trained for the value that is determined with different historical cancer patients with the same type of cancer. Additionally, the tensor fusion can learn based on each new patient whose data undergoes the fusion. For example, the tensor fusion process can perform end-to-end multimodal learning with multimodal tensors as input supervised by a previously-determined objective (e.g., the diagnosis, the prognosis, the therapeutic response profile, or the like for the certain type of cancer). At 414, a feature related to the value can be output.

EXPERIMENTAL

This Experiment demonstrates Pathomic Fusion, an algorithm that fuses different types of data (e.g., histology image, cell graph, and genomic features) into a multimodal tensor that explicitly models bimodal and trimodal interactions from each modality. The multimodal tensor can be used in medicine for fine-grained patient stratification and interpreted for finding prognostic features.

The multimodal networks take advantage of recent advances in imaging and sequencing technologies (e.g., RNA-seq and other sequencing technologies) to build objective image-omic assays for cancer diagnosis and prognosis. This approach was validated on glioma and clear cell renal carcinoma (CCRCC) data from the TCGA, a cancer data consortium that contains paired high-throughput genome analysis and diagnostic whole slide images with ground-truth survival outcome and histologic grade labels. Given paired histology and genomic data with known cancer outcomes, the objective is to learn a robust multimodal representation from both modalities that would outperform unimodal representations in supervised learning.

Methods

In Pathomic Fusion, histology features are extracted as two different views: image-based features using Convolutional Neural Networks (CNNs), and graph-based features using Graph Convolutional Networks (GCNs). Both networks would extract similar morphological features, however, cell graphs from histology images are a more explicit feature representation that directly model cell-to-cell interactions and cell community structure. Following the construction of unimodal features, a gating-based attention mechanism was used to control the expressiveness of each feature before constructing the multimodal tensor. The objective of the multimodal tensor is to capture the space of all possible interactions between features across all modalities, with the gating-based attention mechanism used to regularize unimportant features.

A. Learning Patient Outcomes from H&E Histology Tissue Images Using Convolutional Neural Networks Anatomic pathology has the ability to reveal the inherent phenotypic intratumoral heterogeneity of cancer, and has been an important tool in cancer prognosis for the past century. Tumor microenvironment features such as high cellularity and microvascular proliferation have been extensively linked to tumor suppressor deficiency genes and angiogenesis, and recognized to have clinical implications in the recurrence and proliferation of cancer. To capture these features, a Convolutional Neural Network (CNN) was trained on 512×512 image regions-of-interest (ROIs) at 20× magnification (0.5 µm/pixel) as representative regions of cancer pathology. The network architecture of this CNN is VGG19 with batch normalization, which was finetuned using pre-existing weights trained on ImageNet. A $h_i \in R^{32 \times 1}$ embedding was extracted from the last hidden layer of the Histology CNN, which was used as input into Pathomic Fusion. This network is supervised by the Cox partial likelihood loss for survival outcome prediction, and cross entropy loss for grade classification.

B. Learning Morphometric Cell and Graph Features Using Graph Convolutional Networks The spatial heterogeneity of cells in histopathology has potential in informing the invasion and progression of cancer and in bioinformatics tasks of interest such as cancer subtyping, biomarker discovery and survival outcome prediction. Unlike image-based feature representation of histology tissue using CNNs, cell graph representations explicitly capture only pre-selected features of cells, which can be scaled to cover larger regions of histology tissue.

Let $G=(V,E)$ denote a graph with nodes V and edges E. $X \in R^{N \times F}$ is defined as a feature matrix of N nodes in V with F-dimensional features, and $A \in R^{N \times N}$ as the adjacency matrix that holds the graph topology. To construct graphs that would capture the tumor microenvironment (FIG. 6), on the same histology ROI used as input to the CNN, one must: 1): perform semantic segmentation to detect and spatially localize cells in a histopathology region-of-interest to define a set of nodes V, 2): use K-Nearest Neighbors to find connections between adjacent cells to define a set of edges E, 3): calculate handcrafted and deep features for each cell that would define the feature matrix X, and 4): use graph convolutional networks to learn a robust representation of the entire graph for survival outcome prediction.

Nuclei Segmentation: Accurate nuclei segmentation is important in defining abnormal cell features such as nuclear atypia, abundant tumor cellularity, and other features that would be indicative of cancer progression. Previous works rely on conventional fully convolutional networks that minimize a pixel-wise loss, which can cause the network to segment multiple nuclei as one, leading to inaccurate feature extraction of nuclei shape and community structure. To overcome this issue, the same conditional generative adversarial network (cGAN) was used from the previous work to learn an appropriate loss function for semantic segmentation, which circumvents manually engineered loss functions. As described in previous work, the conditional GAN framework consists of two networks (a generator G and a discriminator D) that compete against each other in a min-max game to respectively minimize and maximize the objective minG maxD L (G, D). Specifically, G is a segmentation network that learns to translate histology tissue images n into realistic segmentation masks m, and D is a binary classification network that aims to distinguish real and predicted pairs of tissue ((n,m) vs. (n,S (n)). The generator is supervised with a L1 loss and adversarial loss function, in which the adversarial loss penalizes the generator for producing segmentation masks that are unrealistic.

$$\mathcal{L}_{GAN}(S, D_M) = $$

$$\mathbb{E}_{m,n \sim p_{data}(m,n)}[\log D_M(m, n)] + \mathbb{E}_{n \sim p_{data}(n)}[\log(1 - D_M(m, S(n)))]$$

Figure 6:
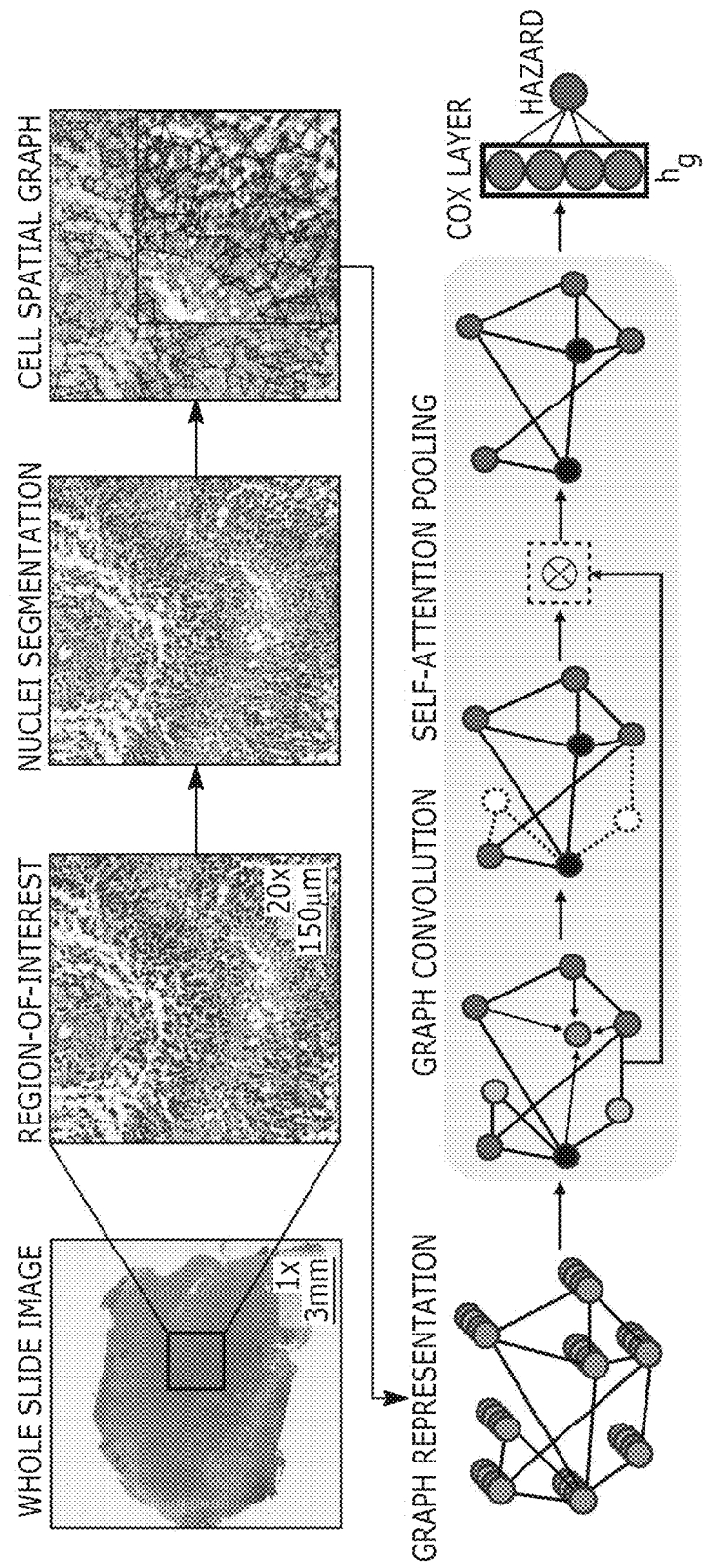
FIG. 6 is an illustration of a graph convolutional network for learning morphometric cell features from histology images.

Cell Graph Construction: From the segmented nuclei, the K-Nearest Neighbors (KNN) algorithm was used from the Fast Library for Approximate Nearest Neighbours (FLANN) library to construct the edge set and adjacency matrix of the graph (FIG. 6). The adjacent cells were hypothesized to have the most significant cell-cell interactions, so the adjacency matrix was limited to K nearest neighbors. In in this experiment, it was assumed that K=5 to detect community structure and model cellular interactions. Using KNN, the adjacency matrix A is defined as:

$$A_{ij} \begin{cases} 1 & \text{if } j \in KNN(i) \text{ and } D(i, j) < d \\ 0 & \text{otherwise} \end{cases}$$

Manual Cell Feature Extraction: For each cell, eight contour features (major axis length, minor axis length, angular orientation, eccentricity, roundness, area, and solidity) were computed, as well as four texture features from gray-level co-occurrence matrices (GLCM) (dissimilarity, homogeneity, angular second moment, and energy). Contours were obtained from segmentation results in nuclei segmentation, and GLCMs were calculated from 64×64 image crops centered over each contour centroid. These twelve features were selected for inclusion in the feature matrix X, as they would describe abnormal morphological features about glioma cells such as atypia, nuclear pleomorphism, and hyperchromatism.

Unsupervised Cell Feature Extraction using Contrastive Predictive Coding: Besides manually computed statistics, an unsupervised technique known as contrastive predictive coding (CPC) was also used to extract 1024-dimensional features from tissue regions of size 64×64 centered around each cell in a spatial graph. Given a high-dimensional data sequence {xt} (256×256 image crop from the histology ROI), CPC was designed to capture high-level representations shared among different portions (64×64 image patches) of the complete signal. The encoder network gene transformed each data observation xi into a low-dimensional representation zi and learned via a contrastive loss whose optimization leads to maximizing the mutual information between the available context ct, computed from a known portion of the encoded sequence {zi},i s t and future observations zt+k, k>0. By minimizing the CPC objective, rich feature representations shared among various tissue regions that are specific to the cells in the underlying tissue site were learned. Examples include the morphology and distinct arrangement of different cell types, inter-cellular interactions, and the microvascular patterns surrounding each cell. To create CPC features for each cell, 64×64 image patches centered over the centroid of each cell were encoded. These features are concatenated with the handcrafted features during cell graph construction.

Graph Convolutional Networks: Similar to CNNs, GCNs learn abstracts feature representations for each feature in a node via message passing, in which nodes iteratively aggregate feature vectors from their neighborhood to compute a new feature vector at the next hidden layer in the network. The representation of an entire graph can be obtained through pooling over all the nodes, which can then be used as input for tasks such as classification or survival outcome prediction. Such convolution and pooling operations can be defined as follows:

$$a_v^{(k)} = \text{AGGREGATE}^{(k)}(\{h_u^{(k-1)} : u \in \mathcal{N}(v)\})$$

$$h_v^{(k)} = \text{COMBINE}^{(k)}(h_v^{(k-1)}, a_v^{(k)})$$

where $h_v^k$ is the feature vector of node v at the k−1-th iteration of the neighborhood aggregation, $a_v^k$ is the feature vector of node v at the next iteration, and AGGREGATE and COMBINE are functions for combining feature vectors between hidden layers. The definitions for AGGREGATE and COMBINE are adopted from GraphSAGE, which for a given node represents the next node hidden layer as the concatenation of the current hidden layer with the neighborhood features:

$$a_v^{(k)} = \text{MAX}(\{\text{RELU}(W \cdot h_u^{(k-1)}), \forall u \in \mathcal{N}(v)\}).$$

$$h_v^{(k)} = W \cdot [h_v^{(k-1)}, a_v^{(k)}].$$

Unlike other graph-structured data, cell graphs exhibit a hierarchical topology, in which the degree of eccentricity and clustered components of nodes in a graph define multiple views of how cells are organized in the tumor microenvironment: from fine-grained views such as local cell-to-cell interactions, to coarser-grained views such as structural regions of cell invasion and metastasis. In order to encode the hierarchical structure of cell graphs, the self-attention pooling strategy SAGPOOL, which is a hierarchical pooling method that performs local pooling operations of node embeddings in a graph, was adopted. In attention pooling, the contribution of each node embedding to the pooling receptive field to the next network layer is adaptively learned using an attention mechanism. The attention score $Z \in \mathbb{R}^{N \times 1}$ for nodes in G can be calculated as such:

$$Z = \sigma(\text{SAGEConv}(X, A + A^2))$$

where X are the node features, A is the adjacency matrix, and SAGEConv is the convolution operator from GraphSAGE. To also aggregate information from multiple scales in the nuclei graph topology, a hierarchical pooling strategy was also adopted. Since the cell graphs are constructed on the entire image, no patch averaging of predicted hazards needs to be performed. At the last hidden layer of the Graph Convolutional SNN, the node features were pooled into $h_g \in \mathbb{R}^{32 \times 1}$ feature vector, which was used as an input to Pathomic Fusion.

C. Predicting Patient Outcomes from Molecular Profiles using Self-Normalizing Networks Advances in next-generation sequencing data have allowed for the profiling of transcript abundance (RNA-Seq), copy number variation (CNV), mutation status, and other molecular characterizations at the gene level, and have been frequently used to study survival outcomes in cancer. For example, isocitrate dehydrogenase 1 (IDH1) is a gene that is important for cellular metabolism, epigenetic regulation and DNA repair, with its mutation associated with prolonged patient survival in cancers such as glioma. Other genes include EGFR, VEGF and MGMT, which are implicated in angiogenesis, the process of blood vessel formulation that also allows cancer to proliferate to other areas of tissue.

Figure 5:
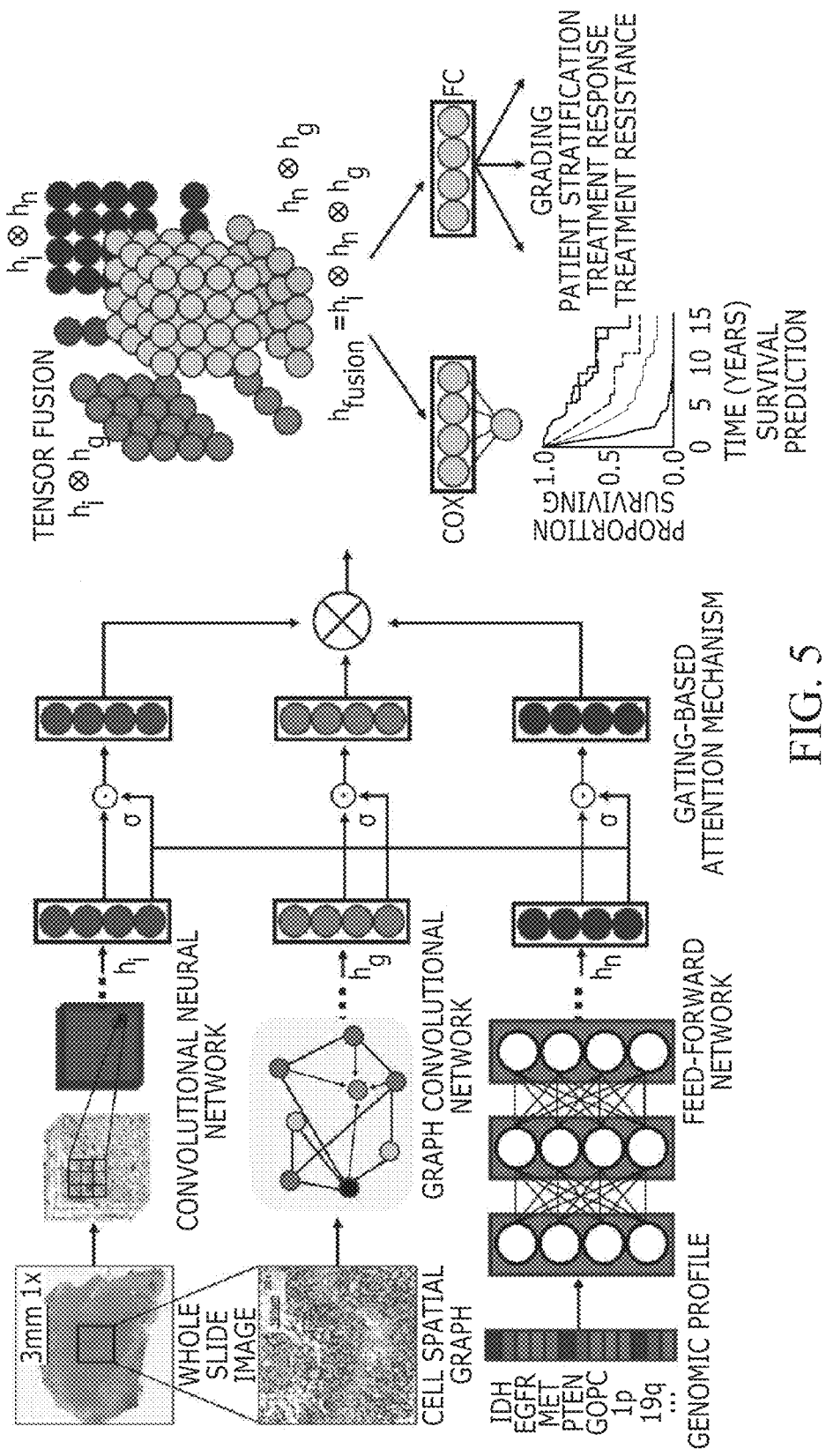
FIG. 5 is a general illustrations of Pathomic Fusion, an integrated framework for multimodal fusion of histology and genomic features for survival outcome prediction and classification.

For learning scenarios that have hundreds to thousands of features with relatively few training samples, Feedforward networks are prone to overfitting. Compared to other kinds of neural network architectures such as CNNs, weights in Feedforward networks are shared and thus more sensitive training instabilities from perturbation and regularization techniques such as stochastic gradient descent and Dropout. To mitigate overfitting on high-dimensional low sample size genomics data and employ more robust regularization techniques when training Feedforward networks, normalization layers from Self-Normalizing Networks described by Klambaeur et al. in *Advances in neural information processing systems,* 2017, pp. 971-980 were used. In Self-Normalizing Networks (SNN), rectified linear unit (ReLU) activations are replaced with scaled exponential linear units (SeLU) to drive outputs after every layer towards zero mean and unit variance. Combined with a modified regularization technique (Alpha Dropout) that maintains this self-normalizing property, well-regularized Feedforward networks that would be otherwise prone to instabilities as a result of vanishing or explosive gradients were trained. The network architecture includes four fully-connected layers followed by Exponential Linear Unit (ELU) activation and Alpha Dropout to ensure the self-normalization property. The last fully-connected layer is used to learn a representation $h_n \in \mathbb{R}^{32 \times 1}$, which is used as input into Pathomic Fusion (FIG. 5).

D. Multimodal Tensor Fusion Vis Kronecher Product and Gating-Based Attention

For multimodal data in cancer pathology, there exists a data heterogeneity gap in combining histology and genomic input-histology images are spatial distributed as (R, G, B) pixels in a two-dimensional grid, whereas cell graphs are defined as a set of nodes V with different sized neighborhoods and edges V, and genomic data is often represented as a one-dimensional vector of covariates. The motivation for multimodal learning is that the inter-modality interactions between histology and genomic features would be able to improve patient stratification into subtypes and treatment groups. For example, in the refinement of histogenesis of glioma, though morphological characteristics alone do not correlate well with patient outcomes, their semantic importance in drawing decision boundaries is changed when conditioned on genomic biomarkers such as IDH1 mutation status and chromosomal 1p19q arm codeletion.

In this work, the aim is to explicitly capture these important interactions using the Kronecker Product, which model feature interactions across unimodal feature representations, that would otherwise not be explicitly captured in feedforward layers. Following the construction of the three unimodal feature representations in the previous subsections, a multimodal representation is built using the Kronecker product of the histology image, cell graph, and genomic features ($h_i$, $h_g$, $h_n$). The joint multimodal tensor computed by the matrix outer product of these feature vectors would capture important unimodal, bimodal and trimodal interactions of all features of these three modalities, shown in FIG. 5 and in the equation below:

$$h_{fusion} = \begin{bmatrix} h_i \\ 1 \end{bmatrix} \otimes \begin{bmatrix} h_g \\ 1 \end{bmatrix} \otimes \begin{bmatrix} h_n \\ 1 \end{bmatrix}$$

where $\otimes$ is the outer product, and hfusion is a differential multimodal tensor that forms in a 3D Cartesian space. In this computation, every neuron in the last hidden layer in the CNN is multiplied by every other neuron in the last hidden layer of the SNN, and subsequently multiplied with every other neuron in the last hidden layer of the GCN. To preserve unimodal and bimodal feature interactions when computing the trimodal interactions, append 1 to each unimodal feature representation. For feature vectors of size [33×1], [33×1] and [33×1], the calculated multimodal tensor would have dimension [33×33×33], where the unimodal features ($h_i$, $h_g$, $h_n$) and bimodal feature interactions ($h_i \otimes h_g$, $h_g \otimes h_n$, $h_i \otimes h_n$) are defined along the outer dimension of the 3D tensor, and the trimodal interactions (captured as $h_i \otimes h_g \, h_n$) in the inner dimension of the 3D tensor (FIG. 5). Following the computation of this joint representation, a final network is learned using fully-connected layers using the multimodal tensor as input, supervised with the previously defined Cox objective for survival outcome prediction and cross-entropy loss for grade classification. Ultimately, the value of Pathomic Fusion is fusing heterogeneous modalities that have disparate structural dependencies. The multimodal network is initialized with pretrained weights from the unimodal networks, followed by end-to-end fine-tuning of the Histology GCN and Genomic SNN.

To decrease the impact of noisy unimodal features during multimodal training, before the Kronecker Product, a gating-based attention mechanism that controls the expressiveness of features of each modality was employed. In fusing histology image, cell graph, and genomic features, some of the captured features may have high collinearity, in which employing a gating mechanism can reduce the size of the feature space before computing the Kronecker Product. For a modality m with a unimodal feature representation $h_m$, a linear transformation $W_{ign \to m}$ of modalities $h_i$, $h_g$, $h_n$ that would score the relative importance of each feature in m is learned, denoted as $z_m$ by: $h_{m,gated} = z_m * h_m$, $\forall m \in \{i, g, n\}$ where, $h_m = \text{ReLU}(W_m \cdot h_m)$, where $z_m = \sigma(W_{ign \to m} \cdot [h_i, h_g, h_n])$. $z_m$ can be interpreted as an attention weight vector, in which modalities i, g, n attend over each feature in modality m. $W_m$ and $W_{ign \to m}$ are weight matrix parameters learned for feature gating. After taking the softmax probability, the element-wise product of features $h_m$ and scores $z_m$ are taken to calculate the gated representation.

E. Multimodal Interpretability

To interpret the network, both Grad-CAM and Integrated Gradients were modified for visualizing image saliency feature importance across multiple types of input. Grad-CAM is a gradient-based localization technique used to produce visual explanations in image classification, in which neurons whose gradients have positive influence on a class of interest are used to produce a coarse heatmap. Since the last layer of the network is a single neuron for outputting hazard, the target was modified to perform back-propagation on the single neuron. As a result, the visual explanations from the network correspond with image regions used in predicting hazard (values ranging from [−3,3]). For Histology GCN and Genomic SNN, Integrated Gradients (IG), a gradient-based feature attribution method that attributes the prediction of deep networks to their inputs, was used. Similar to previous attribution-based methods such as Layer-wise Relevance Propagation, IG calculates the gradients of the input tensor x across different scales against a baseline xi (zero-scaled), and then uses the Gauss-Legendre quadrature to approximate the integral of gradients.

$$IG_i(x) ::= (x_i - x_i') \times \int_{\alpha=0}^{1} \frac{\partial F(x' + \alpha \times (x - x'))}{\partial x_i} d\alpha$$

To adapt IG to graph-based structures, the nodes in the graph input were treated as the batch dimension, and each node in the graph was scaled by the number of integral approximation steps. With multimodal inputs, the integral of gradients for each data modality can be approximated.

Deep Learning-Based Survival Analysis

Survival analysis is a task that models the time to an event, where the outcome of the event is not always observed. Such events are called censored, in which the date of the last known encounter is used as a lower bound of the survival time. For the task of cancer survival outcome prediction, an uncensored event would be patient death, and a censored event would include either patient survival or last known follow-up.

Let T be a continuous random variable that represents patient survival time, and the survival function $S(t) = P(T \geq t_0)$ be the probability of a patient surviving longer than time $t_0$. The probability that an event occurs instantaneously at a time t (after $t_0$) can be denoted as the hazard function $\lambda(t)$. Integrating the hazard function over the time between t and to gives us the survival function.

$$\lambda(t) = \lim_{\partial t \to 0} \frac{P(t \leq T \leq t + \partial t \mid T \geq t)}{\partial t}, \quad S(t) = \exp\left(-\int_0^t \lambda(x) \partial x\right).$$

The most common semi-parametric approach for estimating the hazard function is the Cox proportion hazards model, which assumes that the hazard function can be parameterized as an exponential linear function $\lambda(t|x) = \lambda_0(t) e^{\beta x}$, where $\lambda_0(t)$ is the baseline hazard that describes how the risk of an event changes over time, $\beta$ are model parameters that describe how the hazard varies with covariates/features X of a patient. In the original model, the baseline hazard $\lambda_0(t)$ is left unspecified, making it difficult to estimate $\beta$, however, the Cox partial log-likelihood can be derived that expresses the likelihood of an event to be observed at time t for $\beta, X$.

$$l(\beta, X) = -\sum_{i \in U}\left(X_i\beta - \log\sum_{j \subset R_i} e^{X_j\beta}\right),$$

$$\frac{\partial l(\beta, X)}{\partial X_i} = \delta(i)\beta - \sum_{i,j \in C_1, U} \frac{\beta e^{X_i\beta}}{\sum_{k \in C_1} e^{X_k\beta}}$$

where U is the set of uncensored patients, $R_i$ is the set of patients whose time of death or last follow-up is later than i. From the partial log-likelihood, $\beta$ can be estimated using iterative optimization algorithms such as Newton-Raphson or Stochastic Gradient Descent. To train deep networks for survival analysis, features from the hidden layer are used as covariates in the Cox model, with the derivative of the partial log-likelihood used as error during back-propagation. To evaluate the performance of networks for survival analysis, the Concordance Index (c-Index), which measures the concordance of ranking of predicted hazard scores with the ground truth survival times of patients is used. To demonstrate how well Pathomic Fusion performs over other models, the c-Index was used as a comparative performance metric to measure how well each model is able to predict hazard scores amongst patients (higher is better). The baseline for clinical practice was using the ground truth molecular subtypes as covariates in a Cox proportional hazard model—the canonical regression technique for modeling survival distributions. P-Values were calculated using the Log Rank Test, which was used to assess low vs. high risk stratification on all datasets, low vs. intermediate and intermediate vs. high (33-66-100 percentile) risk stratification in glioma, and 25-50-75-100 percentile risk stratification in CCRCC.

Experimental Setup

A. Data Description

To validate the proposed multimodal paradigm for integrating histology and genomic features, glioma and clear cell renal cell carcinoma data was collected from the TCGA, a cancer data consortium that contains paired high-throughput genome analysis and diagnostic whole slide images with ground-truth survival outcome and histologic grade labels. For astrocytomas and glioblastomas in the merged TCGA-GBM and TCGA-LGG (TCGA-GBMLGG) project, 1024× 1024 region-of-interests (ROIs) from diagnostic slides were used, and sparse stain normalization was also used to match all images to a standard H&E histology image. Multiple regions-of-interest (ROIs) from diagnostic slides were obtained for some patients, creating a total of 1505 images for 769 patients. 320 genomic features from CNV (79), mutation status (1), and bulk RNA-Seq expression from the top 240 differentially expressed genes (240) were curated from the TCGA and the cBioPortal for each patient. For clear cell renal cell carcinoma in the TCGA-KIRC project manually extracted 512×512 ROIs from diagnostic whole slide images were used. For 417 patients in CCRCC, 3 512×512 40×ROIs per patient were collected, yielding 1251 images total that were similarly normalized with stain normalization. These images were paired with 357 genomic features from CNV of genes with alteration frequency greater than 7% (117) and RNA-Seq from the top 240 differentially expressed genes (240). It should be noted that for TCGA-GBMLGG had approximately 40% of the patients had missing RNA-Seq expression.

B. Quantitative Study

TCGA-GBMLGG: Gliomas are a form of brain and spinal cord tumors defined by both hallmark histopathological and genomic heterogeneity in the tumor microenvironment, as well as response-to-treatment heterogeneity in patient outcomes. The current World Health Organization (WHO) Paradigm for glioma classification stratifies diffuse gliomas based on morphological and molecular characteristics: glial cell type (astrocytoma, oligodendroglioma), IDH1 gene mutation status and 1p19q chromosome codeletion status. WHO Grading is made by the manual interpretation of histology using pathological determinants for malignancy (WHO Grades II, III, and IV). These characteristics form three categories of gliomas which have been extensively correlated with survival: 1) IDH-wildtype astrocytomas (IDHwt ATC), 2) IDH-mutant astrocytomas (IDHmut ATC), and 3) IDH-mutant and 1p/19q-codeleted oligodendrogliomas (ODG). IDHwt ATCs (predominantly WHO grades III and IV) have been shown to have the worst patient survival outcomes, while IDHmut ATCs (mixture of WHO Grades II, III, and IV) and ODGs (predominantly WHO Grades II and III) have more favorable outcomes (listed in increasing order). As a baseline against standard statistical approaches/WHO paradigm for survival outcome prediction, Cox Proportion Hazard Models were trained using age, gender, molecular subtypes and grade as covariates.

In this experimentation, an ablation study comparing model configurations and fusion strategies in a 15-fold cross validation was conducted on two supervised learning tasks for glioma: 1) survival outcome prediction, and 2) cancer grade classification. For each task, six different model configurations were trained from the combination of available modalities in the dataset. First, three different unimodal networks were trained: 1) a CNN for in histology image input (Histology CNN), 2) a GCN for cell graph input (Histology GCN), and 3) a SNN for genomic features input (Genomic SNN). For cancer grade classification, mRNA-Seq expression was not used due to missing data, lack of paired training examples, and because grade is solely determined from histopathologic appearance. After training the unimodal networks, three different configurations of Pathomic Fusion were trained: 1) GCN⊗SNN, 2) CNN⊗SNN, 3) GCN⊗CNN⊗SNN. To test for ensembling, multimodal networks that fused histology data with histology data, and genomic features with genomic features were trained.

This fusion approach was compared to internal benchmarks and the previous state-of-the-art approach for survival outcome prediction in glioma, which concatenates histology ROIs with IDH1 and 1p19q genomic features. To compare with their results, their identical train-test split was used, which was created using a 15-fold Monte Carlo cross-validation. TCGA-KIRC: Clear cell renal cell carcinoma (CCRCC) is the most common type of renal cell carcinoma, originating from cells in the proximal convoluted tubules. Histopathologically, CCRCC is characterized by diverse cystic grown patterns of cells with clear or eosinophilic cytoplasm, and a network of thin-walled "chicken wire" vasculature. Genetically, it is characterized by a chromosome 3p arm loss and mutation status of the von Hippel-Lindau (VHL) gene, which leads to lead to stabilization of hypoxia inducible factors that lead to malignancy. Though CCRCC is well-characterized, methods for staging CCRCC suffer from large intra-observer variability in visual histopathological examination. The Fuhrman Grading System for CCRCC is a nuclear grade that ranges from G1 (round or nuform nuclei with absent nucleoli) to G4 (irregular and multilobular nuclei with prominent nucleoli). At the time of the study, the TCGA-KIRC project used the Fuhrman Grading System to grade CCRCC in severity from G1 to G4, however, the grading system has received scrutiny in having poor overall agreement amongst pathologists on external cohorts. As a baseline against standard statistical approaches, Cox Proportion Hazard Models were trained using age, gender, and grade as covariates.

Similar to the ablation study conducted with glioma, the model configurations and fusion strategies were compared in a 15-fold cross validation on CCRCC, and tested for ensembling effects. In demonstrating the effectiveness of Pathomic Fusion in stratifying CCRCC, the Fuhrman Grade was used as a comparative baseline in survival analysis, however, ablation experiments were not performed on grade classification. Since CCRCC does not have multiple molecular subtypes, subtyping was also not performed, however, analyses on CCRCC patient cohorts was performed with different survival durations (shorter surviving and longer surviving patients).

Evaluation: The method was evaluated with standard quantitative and statistical metrics for survival outcome prediction and grade classification. For survival analysis, all models were evaluated using the Concordance Index (c-Index), which is defined as the fraction of all pairs of samples whose predicted survival times are correctly ordered among all uncensored samples (Table I, II). On glioma and CCRCC respectively, the predicted hazards were separated into 33-66-100 and 25-50-75-100 percentiles as digital grades, which were compared with molecular subtyping and grading. For significance testing of patient stratification, the Log Rank Test was used to measure if the difference of two survival curves is statistically significant. Kaplan-Meir estimates and predicted hazard distribution were used to visualize how models were stratifying patients. For grade classification, the networks were evaluated using Area Under the Curve (AUC), Average Precision (AP), F1-Score (micro-averaged across all classes), F1-Score (WHO Grade IV class only), and show ROC curves.

Results

A. Pathomic Fusion Outperforms Unimodal Networks and the WHO Paradigm

In combining histology image, cell graph, and genomic features via Pathomic Fusion, the approach outperforms Cox models, unimodal networks, and previous deep learning-based feature fusion approaches on image-omic-based survival outcome prediction (Table I, Table 2).

TABLE 1

Concordance Index of Pathomic Fusion and ablation experiments in glioma survival prediction.

| Model | c-Index |
| --- | --- |
| Cox (Age + Gender) | 0.732 ± 0.012* |
| Cox (Grade) | 0.738 ± 0.013* |
| Cox (Molecular Subtype) | 0.760 ± 0.011* |
| Cox (Grade + Molecular Subtype) | 0.777 ± 0.013* |
| Histology CNN | 0.792 ± 0.014* |
| Histology GCN | 0.746 ± 0.023* |
| Genomic SNN | 0.808 ± 0.014* |
| SCNN (Histology Only) | 0.754* |
| GSCNN (Histology + Genomic) | 0.781* |
| Pathomic F. (GCN⊗SNN) | 0.812 ± 0.010* |
| Pathomic F. (CNN⊗SNN) | 0.820 ± 0.009* |
| Pathtomic F. (CNN⊗GCN⊗SNN) | 0.826 ± 0.009* |

*p < 0.05

TABLE 2

Concordance Index of Pathomic Fusion and ablation experiments in CCRCC survival prediction.

| Model | c-Index |
| --- | --- |
| Cox (Age + Gender) | 0.630 ± 0.024* |
| Cox (Grade) | 0.675 ± 0.036* |
| Histology CNN | 0.671 ± 0.023* |
| Histology GCN | 0.646 ± 0.022* |
| Genomic SNN | 0.684 ± 0.025* |
| Pathomic F. (GCN⊗SNN) | 0.688 ± 0.029* |
| Pathomic F. (CNN⊗SNN) | 0.719 ± 0.031* |
| Pathomic F. (CNN⊗GCN⊗SNN) | 0.720 ± 0.028* |

*p < 0.05

On glioma, Pathomic Fusion outperforms the WHO paradigm and the previous state-of-the-art (concatenation-based fusion) with 6.31% and 5.76% improvements respectively, reaching a c-Index of 0.826. In addition, multimodal networks were demonstrated to be able to consistently improve upon their unimodal baselines, with trimodal Pathomic Fusion (CNN⊗GCN⊗SNN) fusion of image, graph, and genomic features having the largest c-Index. Though bimodal Pathomic Fusion (CNN⊗SNN) achieved similar performance metrics, the difference between low-to-intermediate digital grades ([0,33) vs. [33,66) percentile of predicted hazards) was not found to be statistically significant. In incorporating features from GCNs, the p-value for testing difference in [0,33] vs. (33,66] percentiles decreased from 0.103 to 2.68e-03. On CCRCC, similar observations were made with trimodal Pathomic Fusion achieving a c-Index of 0.720 and statistical significance in stratifying patients into low and high risk. Using the c-Index metric, GCNs do not add significant improvement over CNNs alone. However, for heterogeneous cancers such as glioma, the integration of GCNs in Pathomic Fusion may provide clinical benefit in distinguishing survival curves of less aggressive tumors.

These improvements were shown not to be due to network ensembling, as inputting same modality twice into Pathomic Fusion resulted in overfitting. On glioma grade classification, similar improvements were seen with Pathomic Fusion with increases of 2.75% AUC, 4.23% average precision, 4.27% F1-score (micro), and 5.11% (Grade IV) over Histology CNN, which is consistent with performance increases found in multimodal learning literature for conventional vision tasks.

B. Pathomic Fusion Improves Patient Stratification

Figure 9:
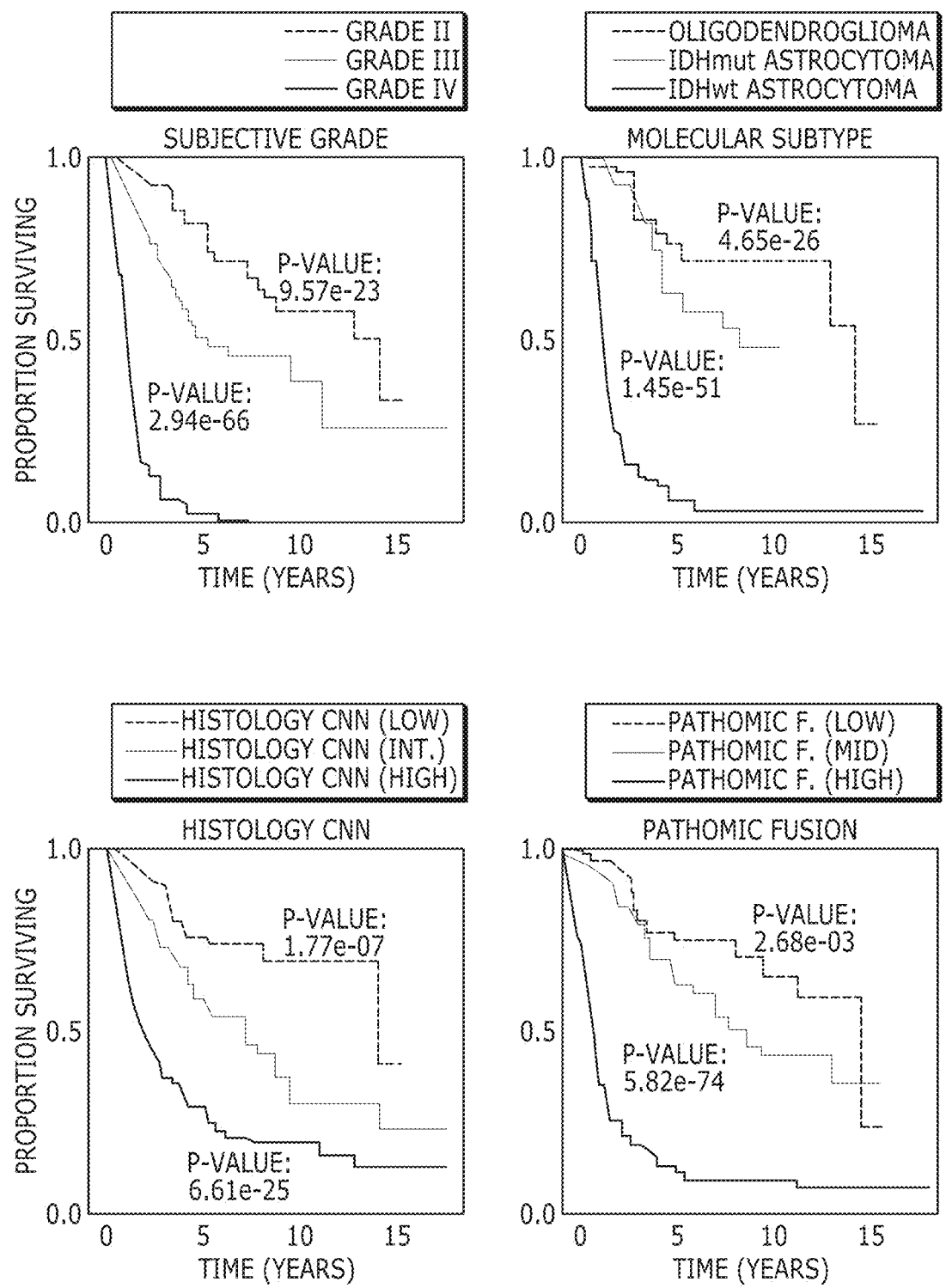
Figure 10:
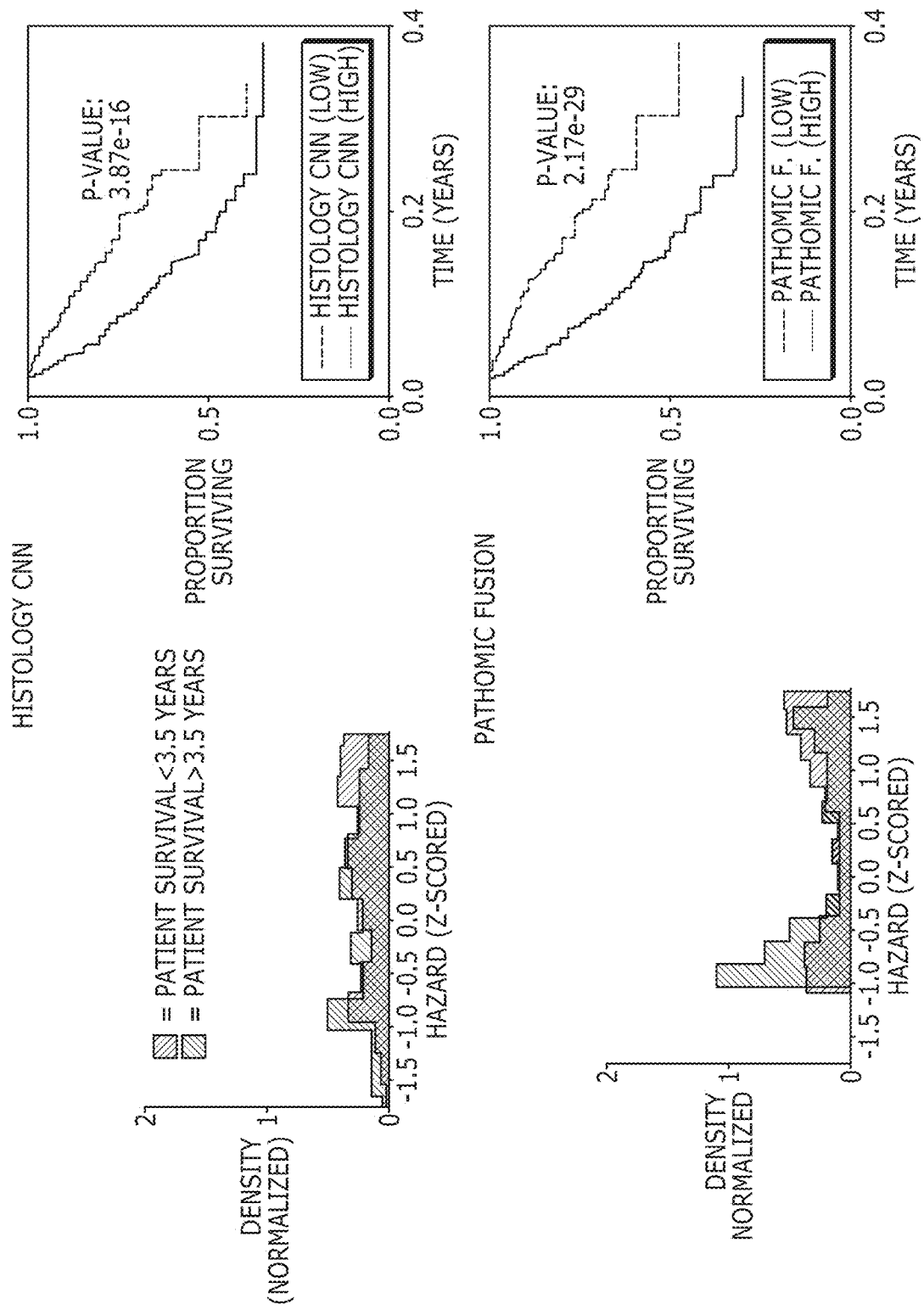
FIG. 10-11 show illustrations related to clear cell renal cell carcinoma (CCRCC)
Figure 11:
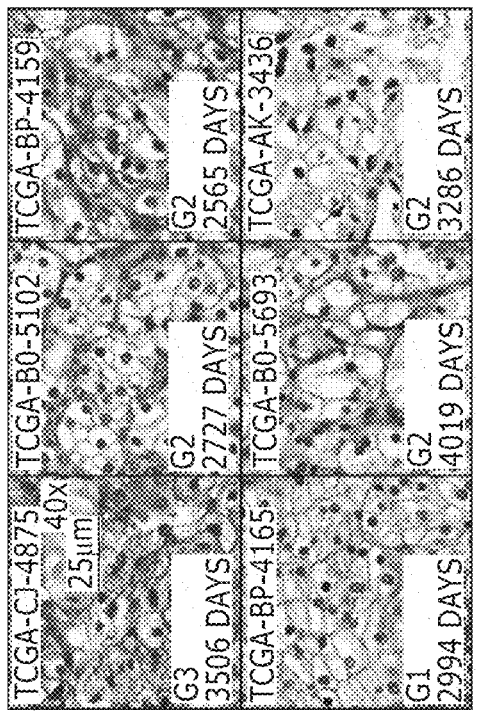
Figure 11:
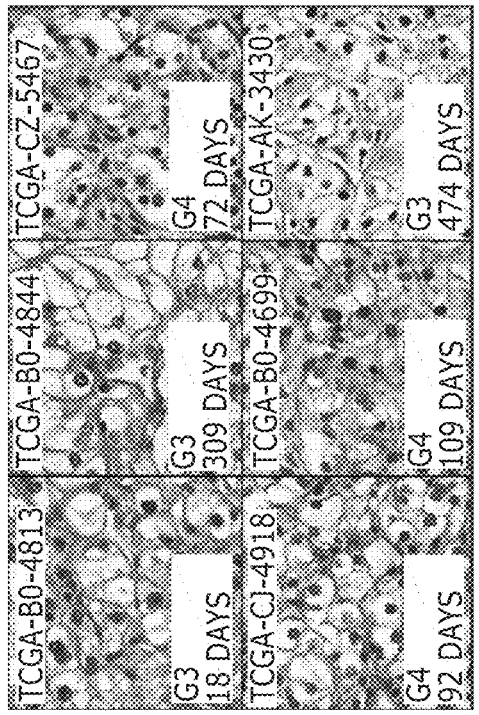
Figure 12:
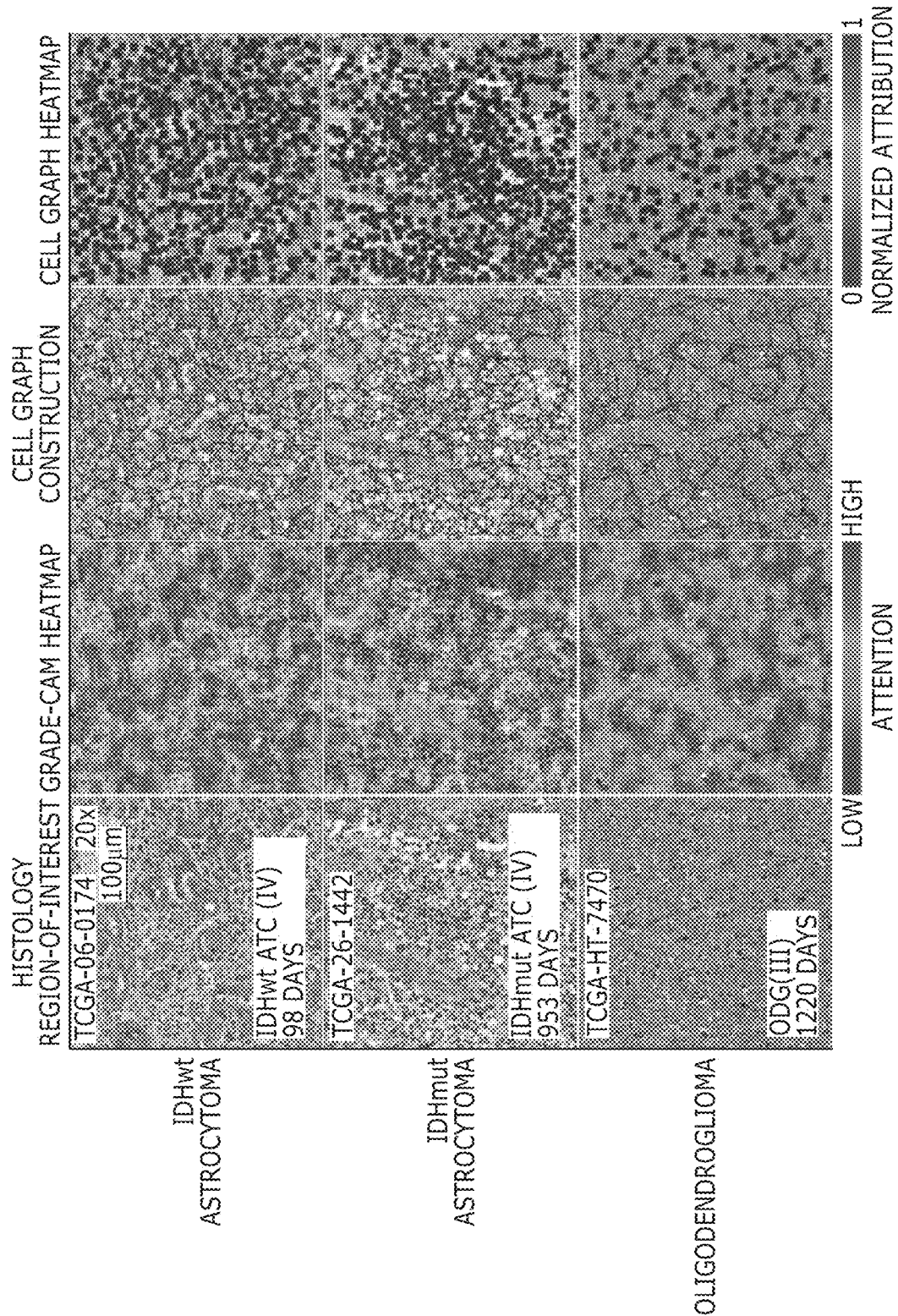
FIG. 12-15 are illustrations of multimodal interpretability by Pathomic Fusion in glioma.
Figure 13:
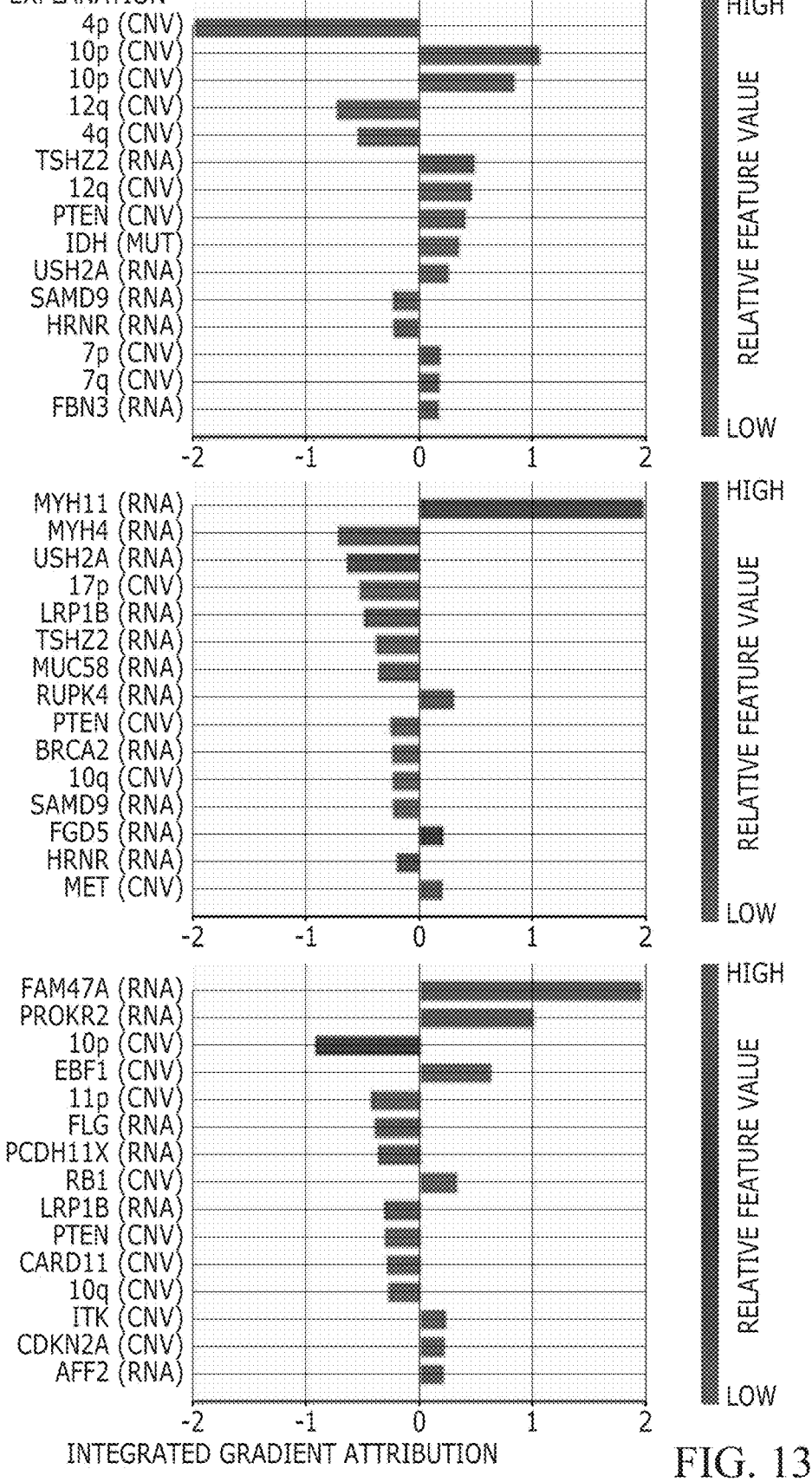
Figure 14:
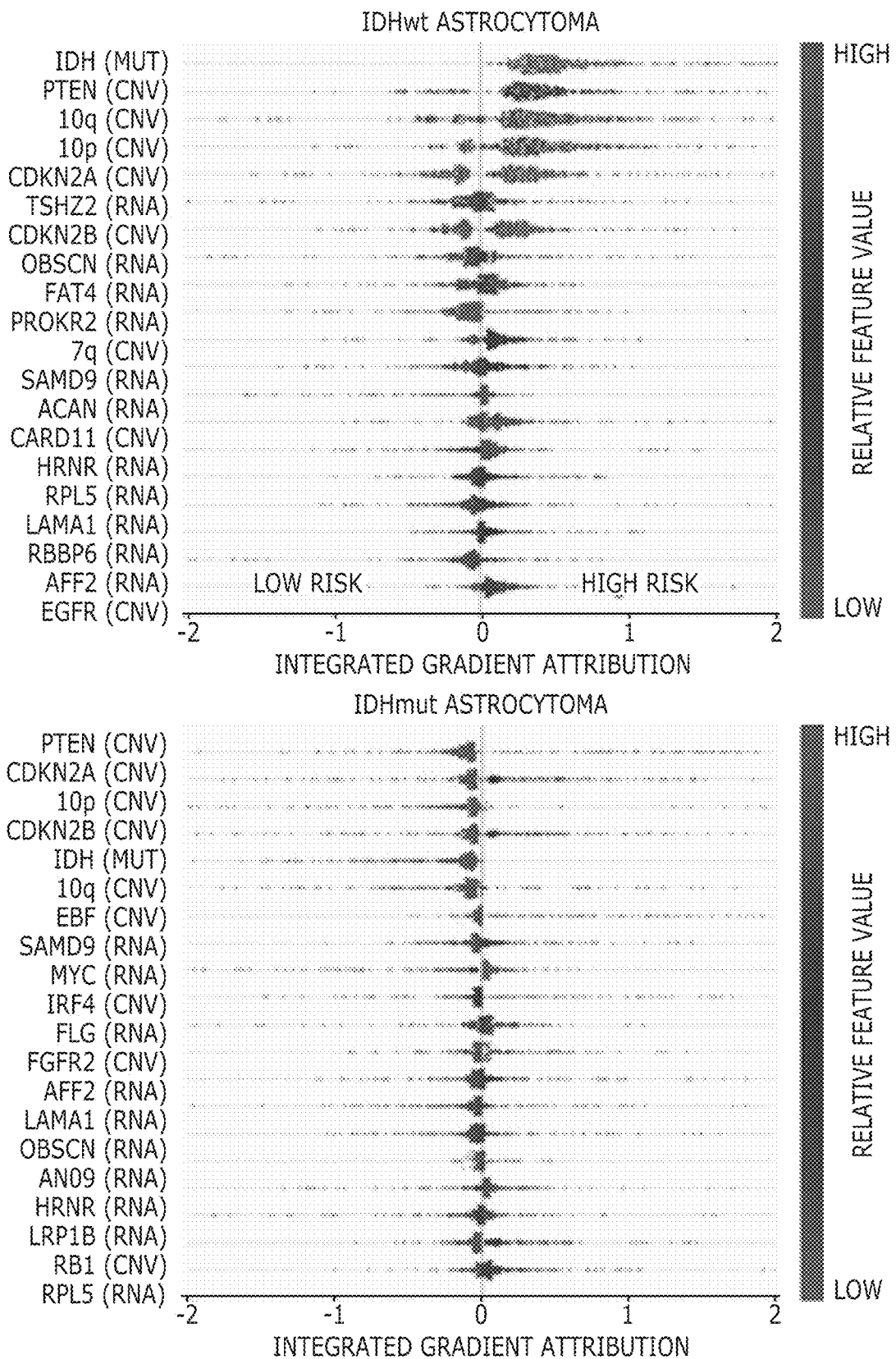
Figure 15:
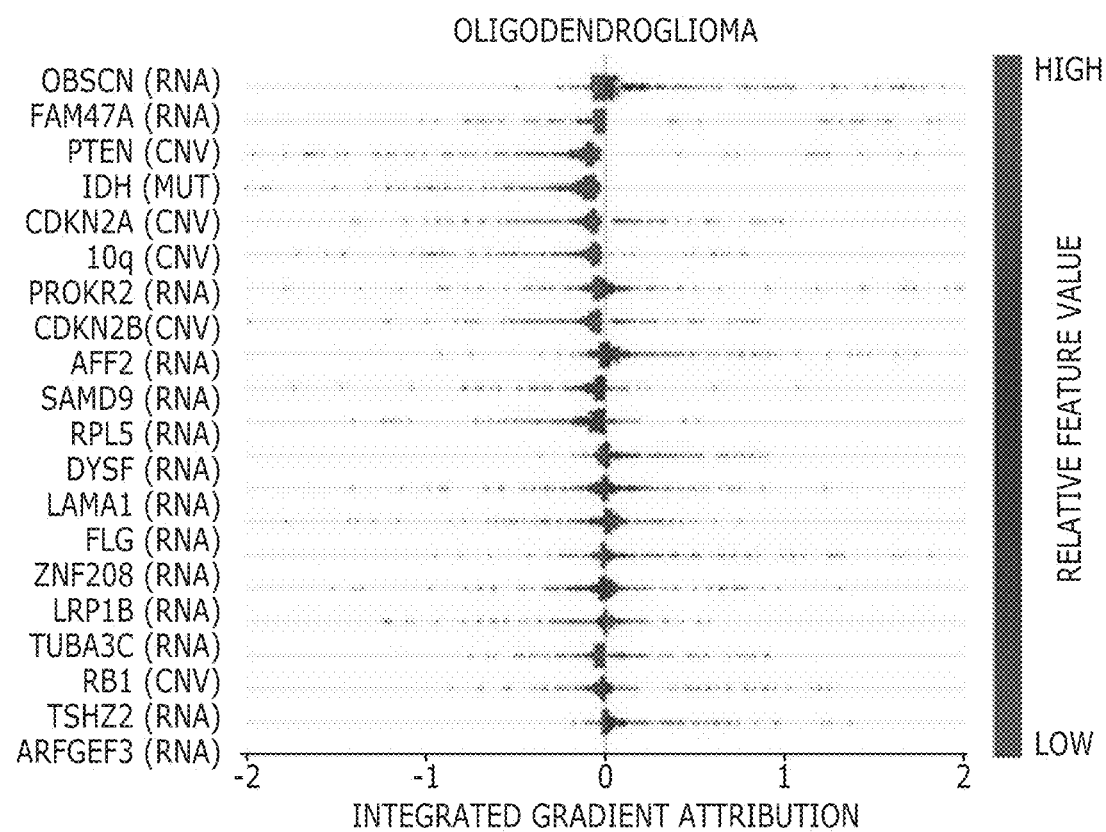
Figure 16:
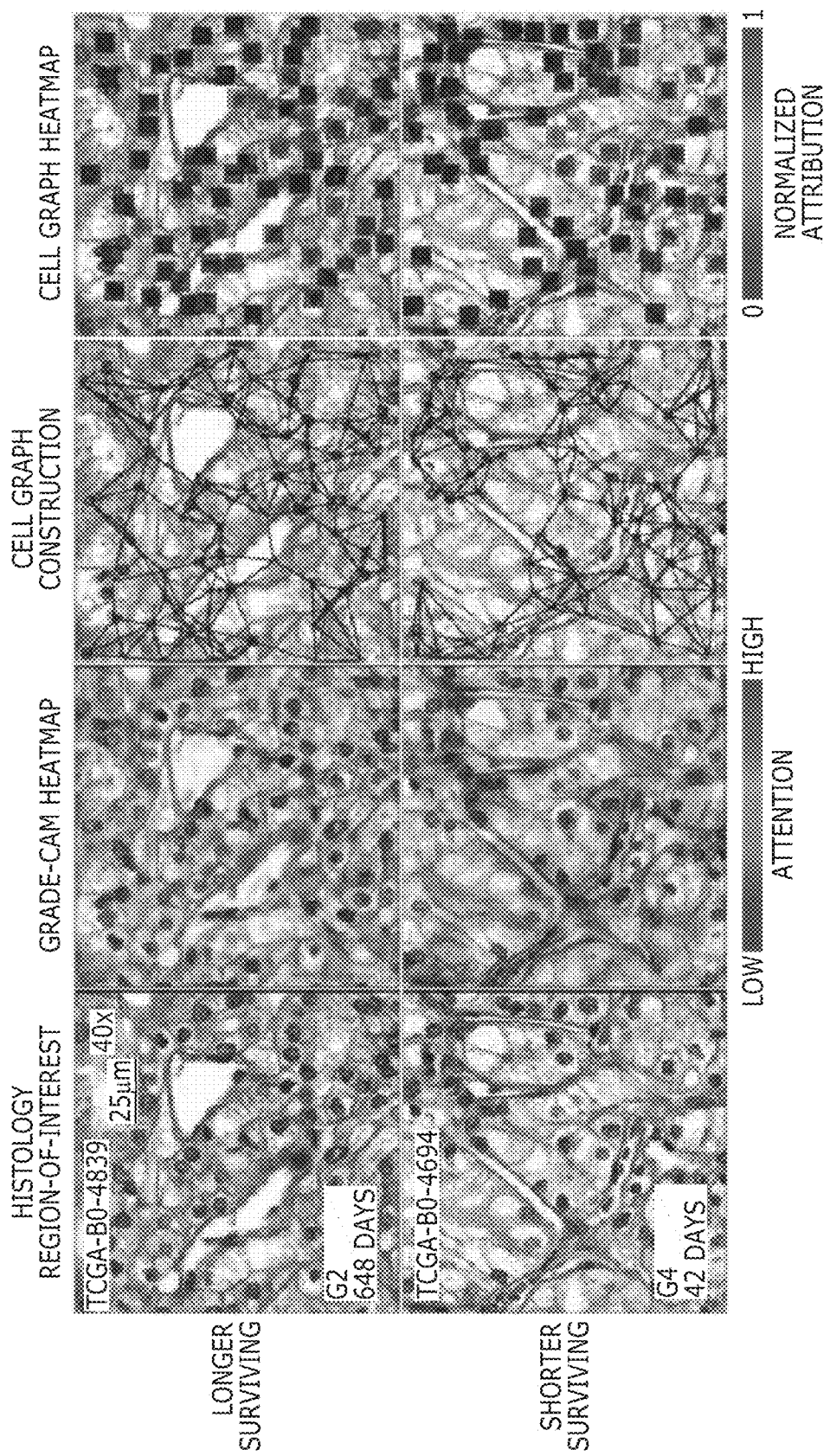
FIG. 16-19 are illustrations of multimodal interpretability by Pathomic Fusion in CCRCC.
Figure 17:
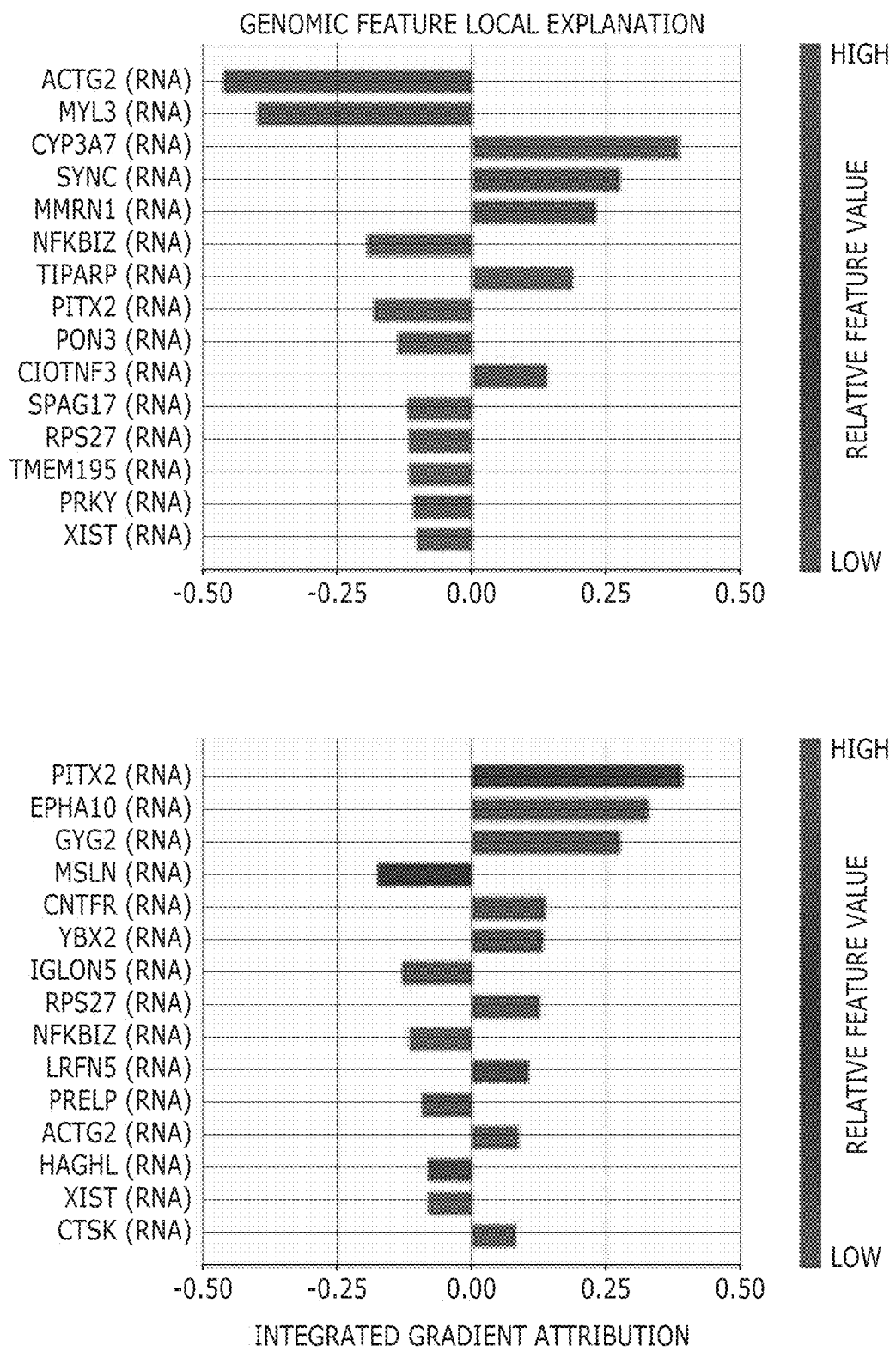
Figure 18:
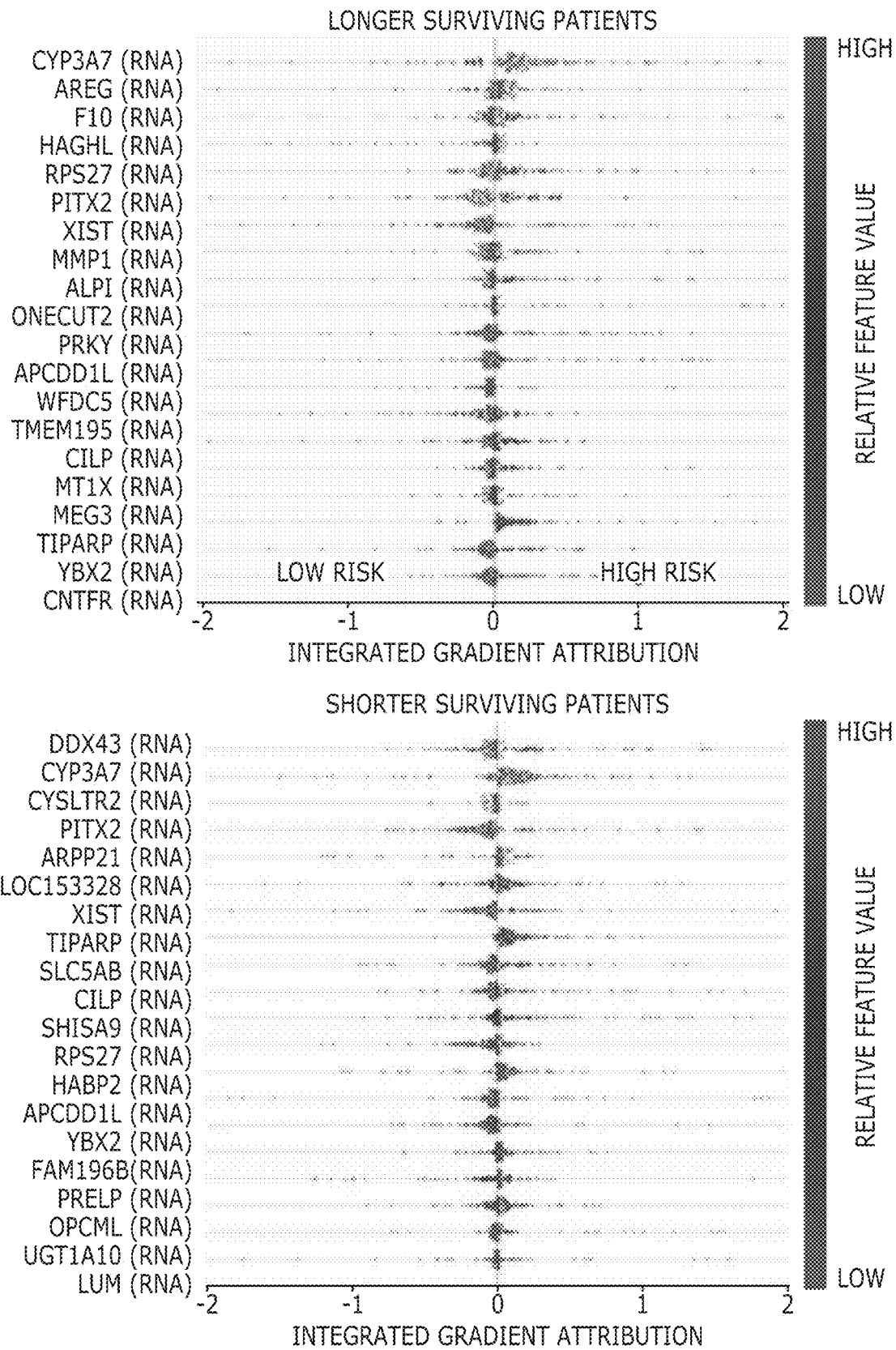
Figure 19:
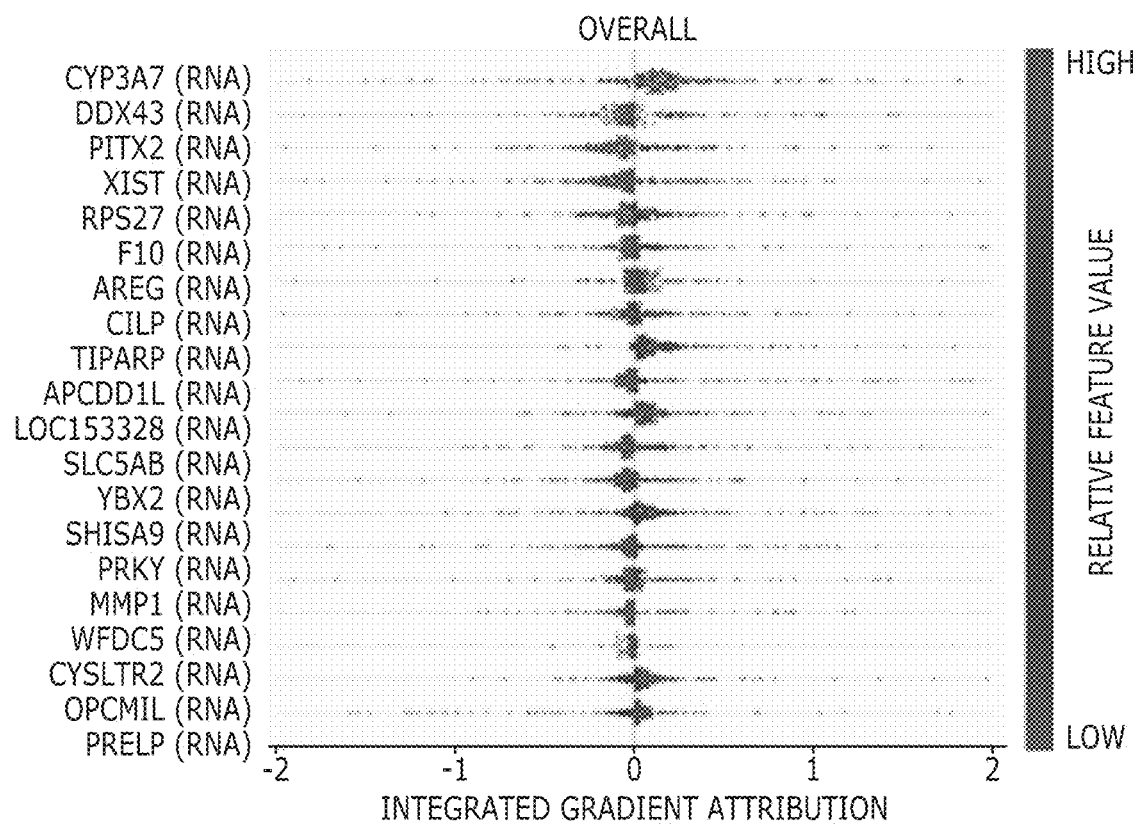

To further investigate the ability of Pathomic Fusion for improving objective image-omic-based patient stratification, Kaplan-Meier (KM) curves of the trained networks were plotted against the WHO paradigm (which uses molecular subtyping) on glioma (FIGS. 7-9), and against the Fuhrman Grading System on CCRCC (FIGS. 10-11). Overall, it was observed that Pathomic Fusion allows for fine-grained stratification of survival curves beyond low vs. high survival, and that these digital grades may be useful in clinical settings in defining treatment cohorts.

Figure 7:
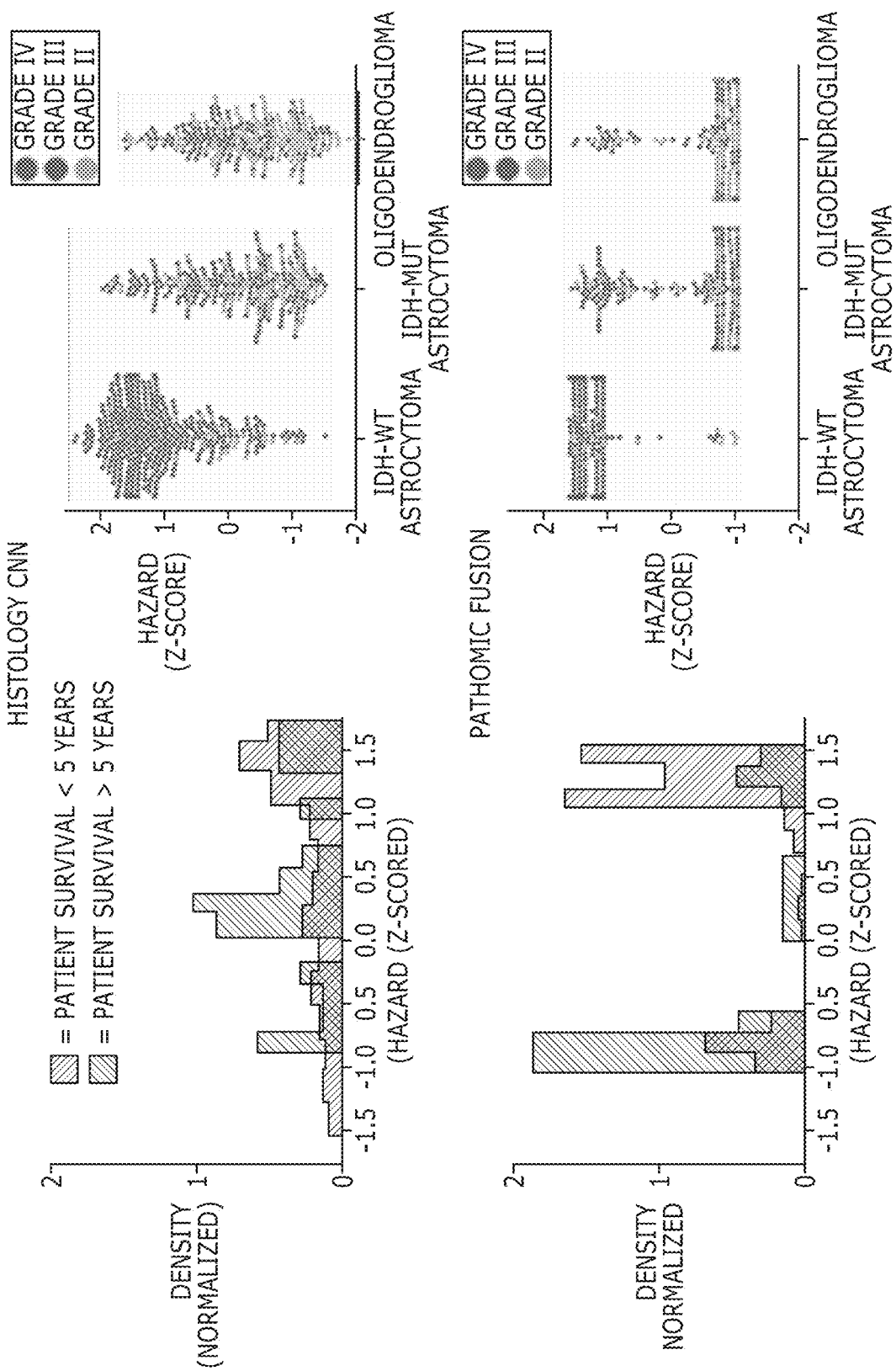
Figure 8:
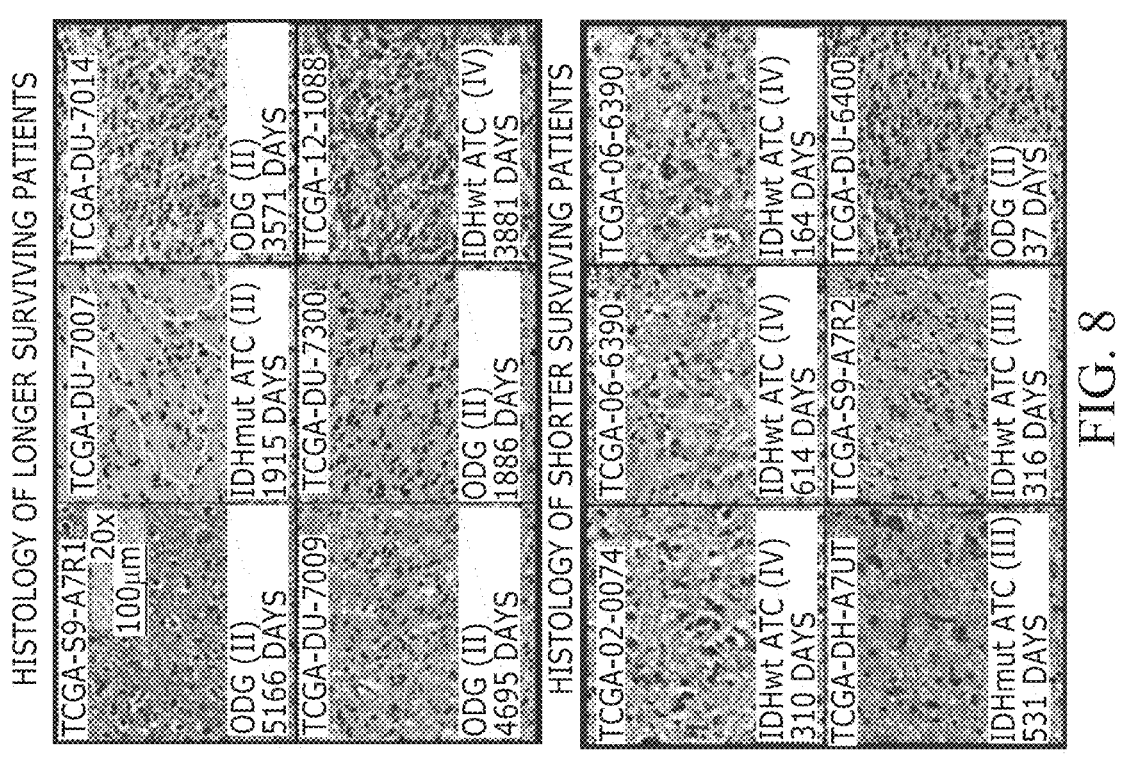

On glioma, similar to, it was observed that digital grading (33-66 percentile) from Pathomic Fusion is similar to that of the three defined glioma subtypes (IDHwt ATC, IDHmut ATC, ODG) that correlate with survival. In comparing Pathomic Fusion to Histology CNN, Pathomic Fusion was able to discriminate intermediate and high risk patients better than Histology CNN. Though Pathomic Fusion was slightly worse in defining low and intermediate risk patients, differences between these survival curves were observed to be statistically significant. Similar confusion in discriminating low-to-intermediate risk patients is also shown in the KM estimates of molecular subtypes, which corroborates with known literature that WHO Grades II and III are more difficult to distinguish than Grades III and IV (FIGS. 7-9). In analyzing the distribution of predicted hazard scores for patients in low vs. high surviving cohorts, it was observed that Pathomic Fusion is able to correctly assign risk to these patients in three high-density peaks/clusters, whereas Histology CNN alone labels a majority of intermediate-to-high risk gliomas with low hazard values. In inspecting the clusters elucidated by Pathomic Fusion ([−1.0,−0.5], [1.0, 1.25] and [1.25, 1.5]), gliomas in these clusters strongly corroborate with the WHO Paradigm for stratifying gliomas into IDHwt ATC, IDHmut ATC, and ODG.

On CCRCC, it was observed that Pathomic Fusion is able to not only differentiate between lower and higher surviving patients, but also assign digital grades that follow patient stratification by the Fuhrman Grading System (FIGS. 10-11). Unlike Histology CNN, Pathomic Fusion is able to disentangle the survival curves of G1-G3 CCRCCs, which have overall low-to-intermediate survival. In analyzing the distribution of hazard predictions by Histology CNN, risk is almost uniformly predicted across shorter and longer survival patients, which suggests that histology alone is a poor prognostic indicator for survival in CCRCC.

C. Multimodal Interpretability of Pathomic Fusion

In addition to improved patient stratification, it was demonstrated that the image-omic paradigm is highly interpretable, in which it can be attributed how pixel regions in histology images, cells in cell graphs, and features in genomic inputs are used in survival outcome prediction.

In examining IG attributions for genomic input, important markers such as IDH wildtype status in glioma and CYP3A7 under-expression in CCRCC correlating with increased risk were corroborated. In glioma, the approach highlights several signature oncogenes such as PTEN, MYC, CDKN2A, EGFR and FGFR2, which are implicated in controlling cell cycle and angiogenesis (FIGS. 12-15). In examining how feature attribution shifts when conditioning on morphological features, several genes become more pronounced in predicting survival across each subtype such as ANO9 and RB1. ANO9 encodes for a protein that mediates diverse physiological functions such as ion transport and phospholipid movement across the membrane. Over-expression of ANO proteins were found to be correlated with poor prognosis in many tumors, which was observed in the IDHmut ATC subtype with decreased ANO9 expression decreases risk. In addition, RB1 over-expression decreases risk also in IDHmut ATC, which corroborates with known literature that RB1 is a tumor suppressor gene. Interestingly, EGFR amplification decreased in importance in IDHwt ATC, which may support evidence that EGFR is not a strong therapeutic target in glioblastoma treatment. In CCRCC, Pathomic Fusion discovers decreased CYP3A7 expression and increased PITX2, DDX43, and XIST expression to correlate with risk, which have been linked to cancer predisposition and tumor progression across many cancers (FIGS. 16-19). In conditioning on morphological features, HAGHL, MMP1 and ARRP21 gene expression becomes more highly attributed in risk prediction. For cancers such as CCRCC that do not have multiple molecular subtypes, Pathomic Fusion has the potential to refine gene signatures in cancers, and uncover new prognostic biomarkers that can be targeted in therapeutic treatments.

Across all histology images and cell graphs in both organ types, it was observed that Pathomic Fusion broadly localizes both vasculature and cell atypia as an important feature in survival outcome prediction. In ATCs, Pathomic Fusion is able to localize not only regions of tumor cellularity and microvascular proliferation in the histology image, but also glial cells between the microvasculature as depicted in the cell graph (FIGS. 12-15). In ODG, both modalities attend towards "fried egg cells", which are mildly enlarged round cells with dark nuclei and clear cytoplasm characteristic in ODG. In CCRCC, Pathomic Fusion attends towards cells with indiscernible nucleoli in longer surviving patients, and large cells with clear nucleoli in shorter surviving patients that is indicative of CCRCC malignancy (FIGS. 16-19). An important aspect about the method is that heatmaps could be leveraged from both histology images and cell graphs to explain prognostic histological features used for prediction. Though visual explanations from the image and cell graph heatmap often overlap in localizing cell atypia, the cell graph can be used to uncover salient regions that are not recognized in the histology image for risk prediction. Moreover, cell graphs may have additional clinical potential in explainability, as the attributions refer to specific atypical cells rather than pixel regions.

From the above description, those skilled in the art will perceive improvements, changes and modifications. Such improvements, changes and modifications are within the skill of one in the art and are intended to be covered by the appended claims.

What is claimed is:

1. A method comprising:
  receiving, by a system comprising a processor, histopathology information comprising at least one whole slide image of at least part of a diseased portion of a subject from a first data source;
  determining, by the system, a first matrix of histology features, wherein the histology features are of a first data type and comprise image-based histology features and graph-based histology features, wherein the first matrix is of a first size, comprising:
    extracting, with a convoluted neural network, the image-based histology features from a region of interest of the histopathology information to reveal any inherent phenotypic intratumoral heterogeneity of the region of interest of the histopathology information; and
    extracting, with a graph convolution network, the graph-based histology features from the region of interest of the histopathology information to reveal spatial heterogeneity of cells in the region of interest;
  receiving, by the system, omics data related to the diseased portion of the subject from a second data source that is different from the first data source;
  determining, by the system, a second matrix of molecular features from the omics data, wherein the molecular features are of a second data type, wherein the second matrix is of a second size;
  fusing, by the system, the first matrix of histology features and the second matrix of molecular features by a tensor fusion process to form a third matrix, wherein the tensor fusion process calculates an outer product space of the histology features and the molecular features and captures the space of all possible interactions between the histology features and the molecular features;
  determining, by the system, a diagnosis, a prognosis, and/or a therapeutic response profile for the diseased portion of the subject based on at least a portion of the third matrix; and outputting, by the system, the diagnosis, the prognosis, and/or the therapeutic response profile for the diseased portion of the subject.

2. The method of claim 1, wherein the fusing further comprises taking a Kronecher product of the first matrix and the second matrix to form the third matrix, wherein the third matrix is a block matrix.

3. The method of claim 1, wherein clustering attention multiple instance learning is used to process an entirety of the whole slide histology image.

4. The method of claim 1, wherein the tensor fusion process creates the third matrix as a joint multimodal tensor cube where every molecular feature is multiplied by every histopathology feature.

5. The method of claim 4, wherein the tensor fusion process performs end-to-end multimodal learning with multimodal tensors as input supervised by a previously defined objective.

6. The method of claim 5, wherein the previously defined objective is the diagnosis, the prognosis, and/or the therapeutic response profile for the diseased portion of the subject.

7. The method of claim 1, wherein the third matrix explicitly models pairwise interactions between the histology features and the molecular features.

8. The method of claim 1, wherein the omics data comprises at least one transcriptome profile.

9. A system comprising:
a computing device comprising:
a memory storing instructions; and
a processor configured to access the memory to execute the instructions to at least:
receive histopathology information comprising at least one whole slide image of at least part of to a diseased portion of a subject from a first data source and omics data related to the diseased portion of the subject from a second data source that is different from the first data source;
determine a first matrix of histology features, wherein the histology features are of a first data type and comprise image-based histology features and graph-based histology features, wherein the first matrix is of a first size, further comprising:
extract, with a convoluted neural network, the image-based histology features from a region of interest of the histopathology information to reveal any inherent phenotypic intratumoral heterogeneity of the region of interest of the histopathology information; and
extract, with a graph convolution network, the graph-based histology features from the region of interest of the histopathology information to reveal spatial heterogeneity of cells in the region of interest;
determine a second matrix of molecular features from the omics data, wherein the molecular features are of a second data type, wherein the second matrix is of a second size;
fuse the first matrix of histology features and the second matrix of molecular features by a tensor fusion process to form a third matrix, wherein the tensor fusion process calculates an outer product space of the histology features and the molecular features and captures the space of all possible interactions between the histology features and the molecular features;
determine a prognosis, and/or a therapeutic response profile for the diseased portion of the subject based on at least a portion of the third matrix; and
output the diagnosis, the prognosis, and/or the therapeutic response profile for the diseased portion of the subject; and
a display device configured to display a parameter related to the diagnosis, the prognosis, and/or the therapeutic response profile for the diseased portion of the subject.

10. The system of claim 9, wherein the histology features and the molecular features are fused by taking a Kronecher product of the first matrix and the second matrix to form the third matrix, wherein the third matrix is a block matrix.

11. The system of claim 9, further comprising at least one of:
a histopathology apparatus configured to provide the histopathology information related to a diseased portion of a subject, wherein the histopathology apparatus is the first data source; and
an omics apparatus configured to provide the omics data related to the diseased portion of the subject, wherein the omics apparatus is the second data source.

12. The system of claim 11, wherein at least two of the computing device, the histopathology apparatus, and the omics apparatus are embodied within a single device.

13. The system of claim 9, wherein the tensor fusion process creates the third matrix as a joint multimodal tensor cube where every molecular feature is multiplied by every histopathology feature.

14. The system of claim 13, wherein the tensor fusion process performs end-to-end multimodal learning with multimodal tensors as input supervised by a previously defined objective.

15. The system of claim 14, wherein the previously defined objective is the diagnosis, the prognosis, and/or the therapeutic response profile for the diseased portion of the subject.

16. The system of claim 9, wherein pairwise interactions between the histology features and the molecular features are examined to determine the third matrix.

17. The system of claim 11, wherein the omics data comprises at least one transcriptome profile.

* * * * *